United States Patent
Sclare et al.

(10) Patent No.: US 9,687,084 B2
(45) Date of Patent: Jun. 27, 2017

(54) NURSING AND INFANT SUPPORT PILLOW WITH ACCESSORY UNIT

(71) Applicant: KIDS, II, INC., Alpharetta, GA (US)

(72) Inventors: Jacob Sclare, Dacula, GA (US); David Gilbert, Cumming, GA (US); Cary Costello, Lawrenceville, GA (US); Daniel Corso, Atlanta, GA (US); Alex Soriano, Atlanta, GA (US); Joseph Staley, Atlanta, GA (US); Katherine Buchanan, Atlanta, GA (US)

(73) Assignee: KIDS II, INC., Atlanta, GA (US)

( * ) Notice: Subject to any disclaimer, the term of this patent is extended or adjusted under 35 U.S.C. 154(b) by 129 days.

(21) Appl. No.: 14/063,660

(22) Filed: Oct. 25, 2013

(65) Prior Publication Data
US 2014/0090169 A1    Apr. 3, 2014

Related U.S. Application Data

(63) Continuation of application No. 13/303,843, filed on Nov. 23, 2011, which is a continuation-in-part of application No. 13/243,570, filed on Sep. 23, 2011.
(Continued)

(51) Int. Cl.
A47D 13/08    (2006.01)
A47G 9/10    (2006.01)

(52) U.S. Cl.
CPC ......... *A47D 13/083* (2013.01); *A47G 9/1036* (2013.01); *Y10T 29/49826* (2015.01)

(58) Field of Classification Search
CPC .................................................. A47D 13/08
(Continued)

(56) References Cited

U.S. PATENT DOCUMENTS

D33,543 S      11/1900 Hogan
3,480,760 A *  11/1969 Young .................... H05B 3/342
                                                 219/528
(Continued)

FOREIGN PATENT DOCUMENTS

CA    2 505 699    10/2006
CN    101448434    6/2009
(Continued)

OTHER PUBLICATIONS

International Search Report and Written Opinion of the International Searching Authority issued Jan. 26, 2011, in corresponding International Application No. PCT/US2011/053092.
(Continued)

*Primary Examiner* — Fredrick Conley
(74) *Attorney, Agent, or Firm* — Gardner Groff Greenwald & Villanueva, PC

(57) ABSTRACT

Particular infant support or nursing pillows are disclosed, for supporting an infant in a variety of settings by providing a stable surface upon which to rest. Various embodiments include a generally crescent shaped device, including a resilient fill material surrounded by a fabric shell and having a top and a bottom surface connected by a band of uniform width extending vertically and wholly about the perimeter of the pillow. The support pillow may be combined with an accessory device to form a support pillow assembly. An attachment mechanism may be configured to attach the accessory device to the support pillow such that the accessory device is arranged to direct a perceptible effect to at least one of the first arm, the second arm, and the medial region of the support pillow.

25 Claims, 34 Drawing Sheets

Related U.S. Application Data

(60) Provisional application No. 61/386,165, filed on Sep. 24, 2010, provisional application No. 61/416,648, filed on Nov. 23, 2010.

(58) Field of Classification Search
USPC .............................. 5/636, 639, 652, 630, 655
See application file for complete search history.

(56) References Cited

U.S. PATENT DOCUMENTS

| | | | |
|---|---|---|---|
| 3,863,283 A * | 2/1975 | Mohr ..................... B60R 7/00 5/490 |
| 4,136,685 A | 1/1979 | Ramey | |
| 4,173,048 A | 11/1979 | Varaney | |
| 4,335,725 A * | 6/1982 | Geldmacher ........... A61F 7/007 219/202 |
| 4,591,693 A * | 5/1986 | Pike ..................... A47C 21/048 219/201 |
| 4,783,866 A * | 11/1988 | Simmons ............. A47G 9/1036 5/421 |
| 4,859,250 A * | 8/1989 | Buist ....................... F25B 21/02 126/205 |
| 5,168,590 A * | 12/1992 | O'Sullivan ....................... 5/490 |
| 5,224,637 A | 7/1993 | Colombo | |
| 5,313,678 A | 5/1994 | Redewill | |
| 5,553,148 A | 9/1996 | Werle | |
| 5,661,861 A | 9/1997 | Matthews | |
| 5,661,862 A | 9/1997 | Ryndak | |
| 5,664,828 A | 9/1997 | Simon | |
| 5,682,632 A | 11/1997 | Cotroneo | |
| 5,754,998 A | 5/1998 | Selton | |
| 5,790,999 A | 8/1998 | Clark | |
| 5,813,065 A | 9/1998 | Tinhorn | |
| 5,971,761 A | 10/1999 | Tillman, Sr. | |
| 6,026,330 A | 2/2000 | Chuang | |
| 6,038,720 A | 3/2000 | Matthews et al. | |
| 6,052,848 A | 4/2000 | Kelly | |
| 6,070,585 A | 6/2000 | Frey et al. | |
| 6,175,981 B1 | 1/2001 | Lizama et al. | |
| D444,981 S | 7/2001 | Hall et al. | |
| 6,279,185 B1 | 8/2001 | Matthews | |
| 6,625,828 B2 * | 9/2003 | Matthews Brown A47D 13/083 5/490 |
| 6,785,921 B1 | 9/2004 | Conforti | |
| 6,810,545 B1 * | 11/2004 | Darling .................. A47D 13/08 5/630 |
| 6,842,925 B1 | 1/2005 | Owens et al. | |
| D501,349 S | 2/2005 | Harris et al. | |
| 7,146,663 B2 * | 12/2006 | Brown ................. A47D 13/083 5/636 |
| 7,322,061 B2 | 1/2008 | Carrol | |
| D673,410 S | 1/2013 | O'Connell | |
| 2002/0088058 A1 | 7/2002 | Matthews Brown | |
| 2004/0025255 A1 | 2/2004 | Matthews Brown | |
| 2004/0267173 A1 | 12/2004 | Mangano | |
| 2005/0000023 A1 | 1/2005 | Brown et al. | |
| 2006/0265809 A1 | 11/2006 | Wagner | |
| 2007/0022526 A1 * | 2/2007 | Leach ................... A47K 3/127 4/572.1 |
| 2007/0192961 A1 | 8/2007 | Tidwell et al. | |
| 2007/0226910 A1 | 10/2007 | Tidwell | |
| 2007/0256242 A1 | 11/2007 | Warnock | |
| 2012/0073058 A1 | 3/2012 | Sclare et al. | |
| 2012/0131747 A1 | 5/2012 | Sclare et al. | |
| 2013/0198963 A1 | 8/2013 | Sclare et al. | |

FOREIGN PATENT DOCUMENTS

| | | |
|---|---|---|
| DE | 295 19 799 | 6/1996 |
| GB | 2 316 008 | 2/1998 |
| WO | WO 96/14008 | 5/1996 |
| WO | WO 2010/064809 | 6/2010 |

OTHER PUBLICATIONS

Second Written Opinion of the International Searching Authority issued Sep. 27, 2012 in corresponding International Application No. PCT/US2011/053092.
International Search Report and Written Opinion of the International Authority issued Mar. 2, 2012, in corresponding International Application No. PCT/US2011/062112.
Written Opinion of the International Preliminary Examining Authority mailed Feb. 28, 2013, in corresponding International application No. PCT/US2011/062112.
International Preliminary Report on Patentability mailed Aug. 7, 2013, in corresponding International Application No. PCT/US2011/062112.
U.S. Appl. No. 13/303,843—Office Action dated May 24, 2013.
U.S. Appl. No. 13/303,842—Response filed Nov. 13, 2013.
U.S. Appl. No. 13/836,844—Office Action dated May 23, 2013.
U.S. Appl. No. 13/836,844—Response filed Aug. 23, 2013.
U.S. Appl. No. 13/836,844—Office Action dated Oct. 22, 2013.
U.S. Appl. No. 13/243,570—Office Action dated May 23, 2013.
U.S. Appl. No. 13/243,570—Response filed Nov. 13, 2013
U.S. Appl. No. 13/243,570—Final Office Action dated Jan. 7, 2014.
U.S. Appl. No. 13/303,843—Final Office Action dated Jan. 2, 2014.
U.S. Appl. No. 13/243,570—Amendment After Final filed Mar. 4, 2014.
U.S. Appl. No. 13/243,570—Advisory Action dated Mar. 13, 2014.
U.S. Appl. No. 13/303,843—Amendment After Final filed Mar. 3, 2014.
U.S. Appl. No. 13/303,843—Advisory Action dated Mar. 14, 2014.
U.S. Appl. No. 13/303,843—Request for Continued Examination and Amendment filed Apr. 2, 2014.
U.S. Appl. No. 13/836,844—Request for Continued Examination and Amendment filed Jan. 22, 2014.
U.S. Appl. No. 13/836,844—Non-final Office Action dated Mar. 12, 2014.
Search Report for corresponding Chinese Application No. 2011800564865 completed Feb. 13, 2015.
Non-final Office Action for U.S. Appl. No. 13/303,843 dated Feb. 11, 2015.
Search Report for corresponding Chinese Application No. 2010800320654 completed Nov. 25, 2015.

* cited by examiner

NURSING AND INFANT SUPPORT PILLOW WITH ACCESSORY UNIT

CROSS-REFERENCE TO RELATED APPLICATION

This application is a continuation of U.S. patent application Ser. No. 13/303,843; filed Nov. 23, 2011; which is a continuation-in-part of U.S. patent application Ser. No. 13/243,570, filed Sep. 23, 2011; which claims priority to U.S. Provisional Patent Application No. 61/386,165, filed Sep. 24, 2010; and also claims priority to U.S. Provisional Patent Application No. 61/416,648, filed Nov. 23, 2010. The disclosure of each referenced application is hereby incorporated herein in its entirety by reference.

BACKGROUND

Field of the Disclosure

The present disclosure generally provides infant support pillows having increased utility. In particular, the disclosure provides infant support pillows and accessory devices useable therewith.

Description of Related Art

Infant support pillows are differentiated from traditional pillows or support devices in that they are specifically shaped to fit around the torso of a caregiver in order to support an infant while feeding, specifically breast feeding or bottle feeding. Alternately, support pillows may serve the purpose of supporting an infant when placed on his tummy, on his back (semi-reclined), or when seated in an upright position.

It is known to use vibration mechanisms to sooth a child. For example, swings, cribs, infant carriers and other devices may include vibration mechanisms configured to sooth a child. However, there remains a need for an improved infant support pillow that includes an accessory capable of providing a sensory experience, such as a vibration mechanism or other unit configured to provide a perceptible effect, with features configured to enhance the convenience and functionality associated with use of the accessory.

SUMMARY OF THE DISCLOSURE

A support pillow assembly is provided in one embodiment. The support pillow assembly may comprise a support pillow comprising a resilient fill material and a fabric shell at least partially enclosing the fill material. The resilient fill material and the fabric shell may define a first arm, a second arm, and a medial region that connects the first arm to the second arm, wherein the first arm, the second arm, and the medial region at least partially surround and collectively define a well, and wherein the first arm, the second arm, and the medial region define a first substantially laterally-extending support surface and an opposing second laterally-extending support surface. The support pillow assembly may further comprise an accessory device, and an attachment mechanism configured to attach the accessory device to at least one of the first arm, the second arm, and the medial region of the support pillow such that the accessory device is arranged to direct a perceptible effect to at least one of the first arm, the second arm, and the medial region. In some instances, the accessory device is arranged to avoid direct contact with at least the first substantially laterally-extending support surface.

In some embodiments, the attachment mechanism may comprise a first pocket. The attachment mechanism may further comprise a tether configured to couple the accessory device to the support pillow. The attachment mechanism may further comprise a second pocket, and the tether may be configured to allow for insertion of the accessory device in either or both of the first pocket and the second pocket. The first pocket may extend inside of the fabric shell. The first pocket may extend substantially parallel to at least one of the first substantially laterally-extending support surface and the second laterally-extending support surface. In another embodiment the first pocket may be positioned externally to the fabric shell.

In some embodiments the attachment mechanism may further comprise a second pocket, and a distance between the first pocket and the second laterally-extending support surface may differ from a distance between the second pocket and the second laterally-extending support surface. The accessory device may comprise a vibration unit arranged to direct vibrations, as a perceptible effect, to at least one of the first arm, the second arm, and the medial region. Further, the accessory device may comprise a vibration transmitter, which may be detachable from the vibration unit. The vibration transmitter may comprise a first extension configured to transmit vibrations to the first arm of the support pillow, and a second extension configured to transmit vibrations to the second arm of the support pillow. A distance between the first extension and the second extension may be adjustable, for example, so as to allow a size of the well to be adjusted.

In some embodiments the accessory device may further comprise a speaker arranged to direct an audio output to at least one of the first arm, the second arm, and the medial region as the perceptible effect. The vibration unit may be configured to vibrate in synchronization with the audio output from the speaker. Also, the accessory device may comprise a remote controller. The attachment mechanism may comprise a cavity defining an opening at the first substantially laterally-extending support surface. The cavity and the accessory device may be configured such that when the accessory device is received in the cavity, the accessory device is recessed relative to the first substantially laterally-extending support surface, the second laterally-extending surface, and/or a sidewall or band extending about the perimeter of the support pillow.

In some embodiments the accessory device may comprise a plurality of vibration units and one or more controllers each configured to operate one or more of the vibration units (i.e., the vibration units may be independently controlled). The vibration units may or may not be physically interconnected, but may be configured to be controlled by a single controller. The at least one controller may be configured to at least partially independently control the vibration units. The accessory device may comprise a fixed portion that is fixed to the support pillow and a removable portion that may be attached to or removed from the fixed portion. The accessory device may be configured to operate upon attachment of the removable portion to the fixed portion. The removable portion may be configured to hold a battery and/or the removable portion may comprise a vibration mechanism.

In some embodiments the accessory device may comprise a thermal element configured to affect a temperature of at least one of the first arm, the second arm, and the medial region, an aromatic element configured to release a scent through at least one of the first arm, the second arm, and the medial region, and/or a lighting element configured to direct light to at least one of the first arm, the second arm, and the medial region as the respective perceptible effects. The attachment mechanism may comprise a strap fixed to the support pillow or a strap fixed to the accessory device. The attachment mechanism may also comprise a clip coupled to the accessory device and configured to removably or compressively engage the support pillow. The attachment mechanism may also comprise at least one of a magnet, a snap fastener, a zipper, and a hook and loop fastener.

In another embodiment, an accessory device configured for use with a support pillow is provided. The accessory device may comprise the above-described vibration unit configured to produce vibrations in some embodiments.

In an additional embodiment, a method for forming a support pillow assembly is provided. The method may comprise providing a support pillow comprising a resilient fill material and a fabric shell at least partially enclosing the fill material. The resilient fill material and the fabric shell may define a first arm, a second arm, and a medial region that connects the first arm to the second arm. Further, the first arm, the second arm, and the medial region may at least partially surround and collectively define a well. Also, the first arm, the second arm, and the medial region may define a first substantially laterally-extending support surface and an opposing second laterally-extending support surface in some embodiments.

The method may also include providing an accessory device, providing an attachment mechanism, and attaching the accessory device to at least one of the first arm, the second arm, and the medial region of the support pillow with the attachment mechanism such that the accessory device is arranged to direct a perceptible effect to at least one of the first arm, the second arm, and the medial region and/or avoids direct contact with the first substantially laterally-extending support surface.

Other aspects and advantages of the present disclosure will become apparent from the following.

BRIEF DESCRIPTION OF THE FIGURES

Figure 1:
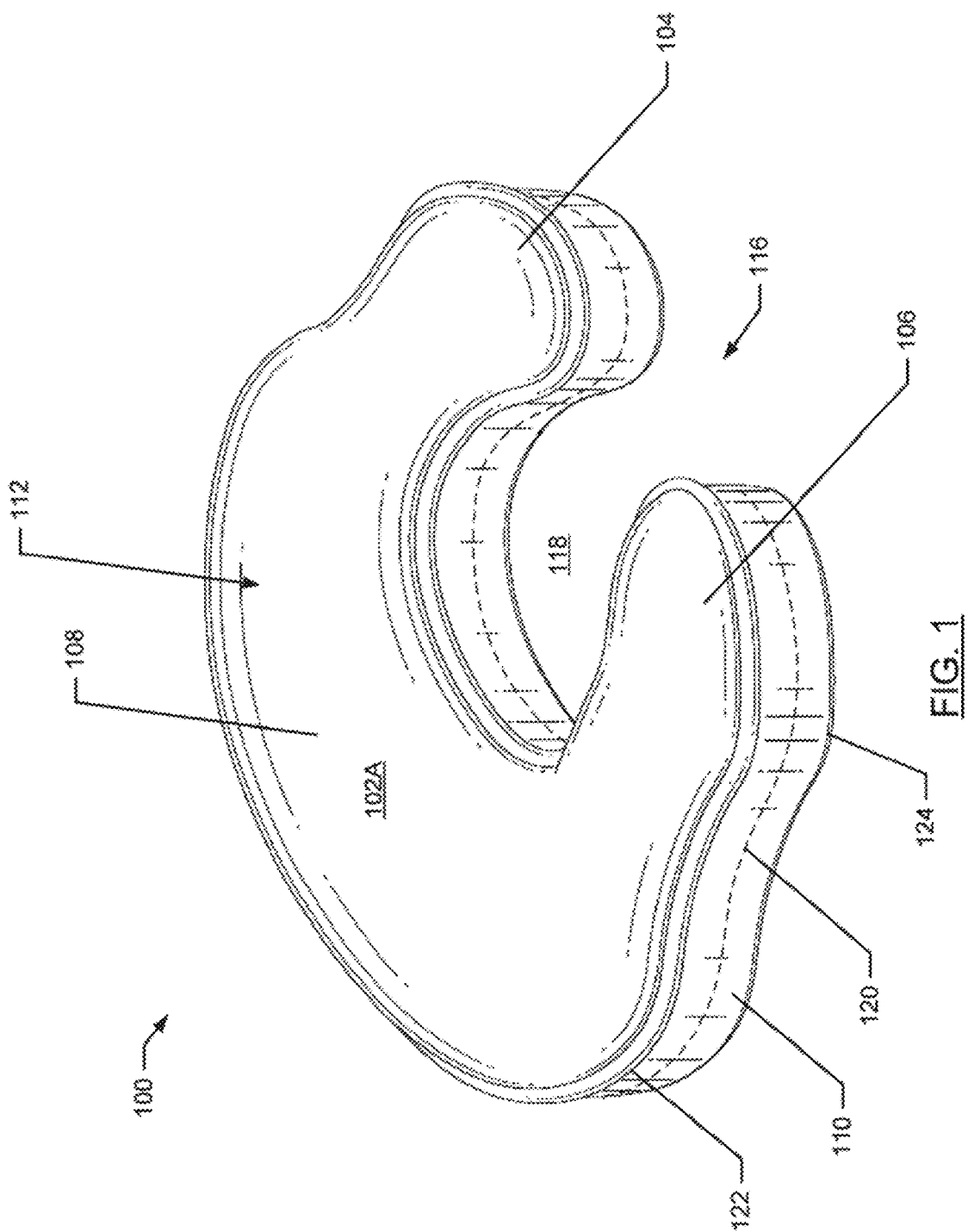
Figure 2:
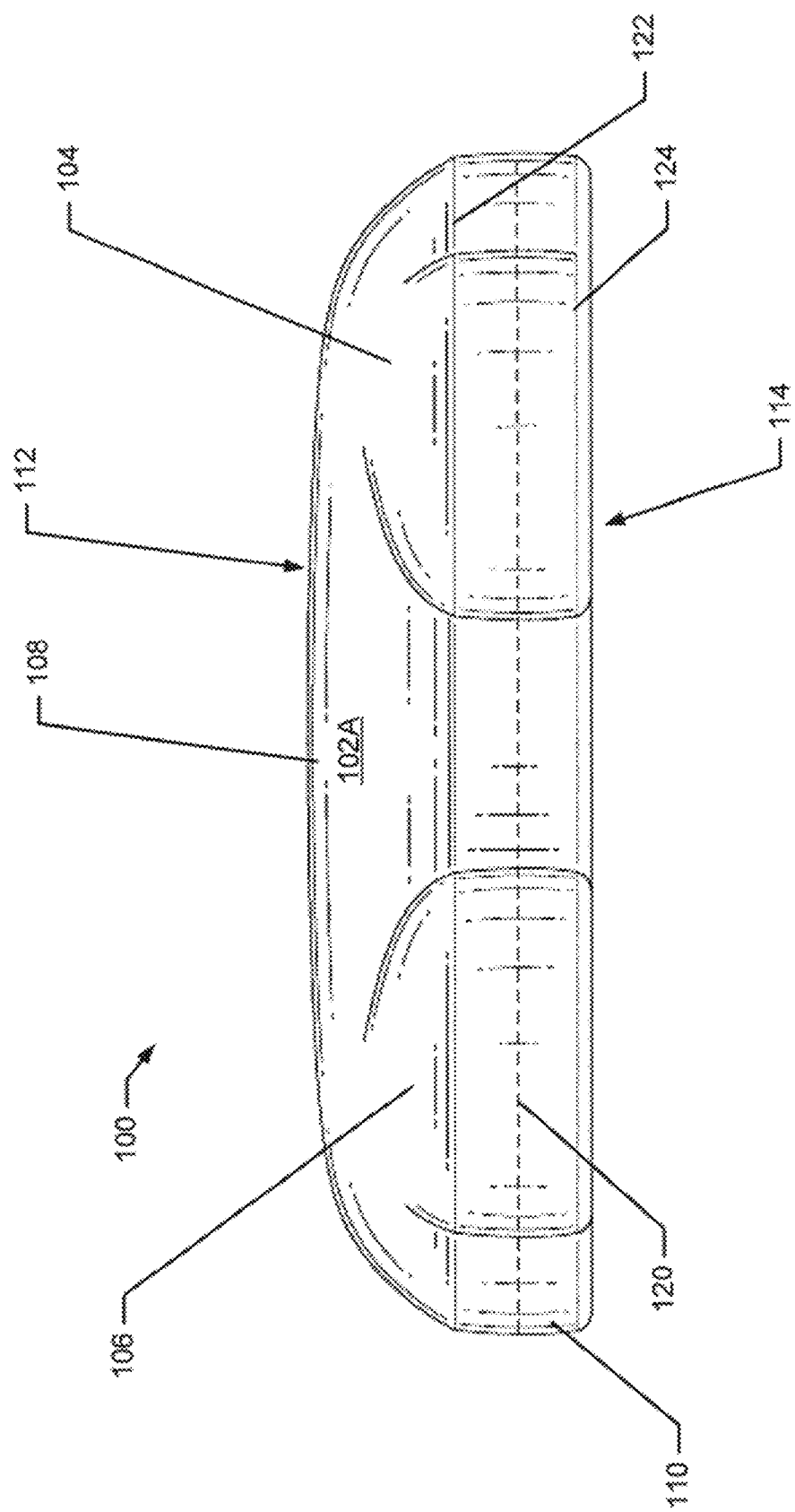
Figure 3:
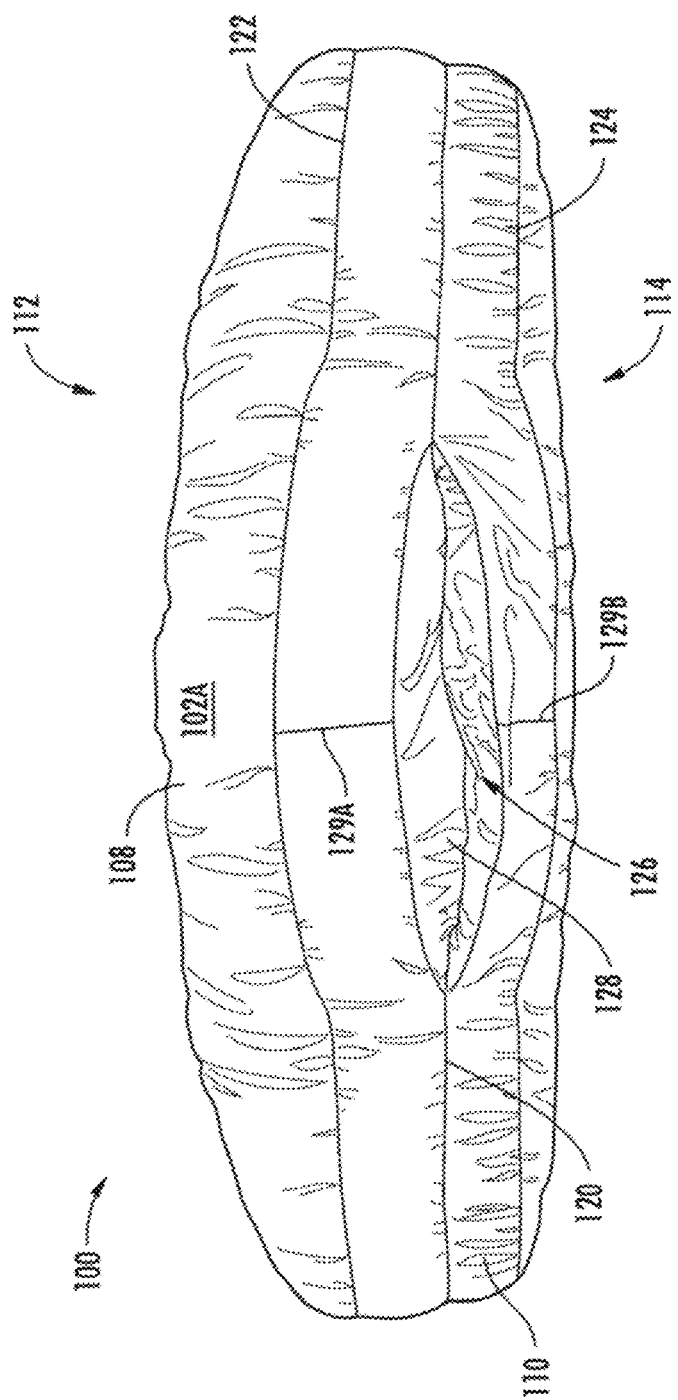
Figure 4:
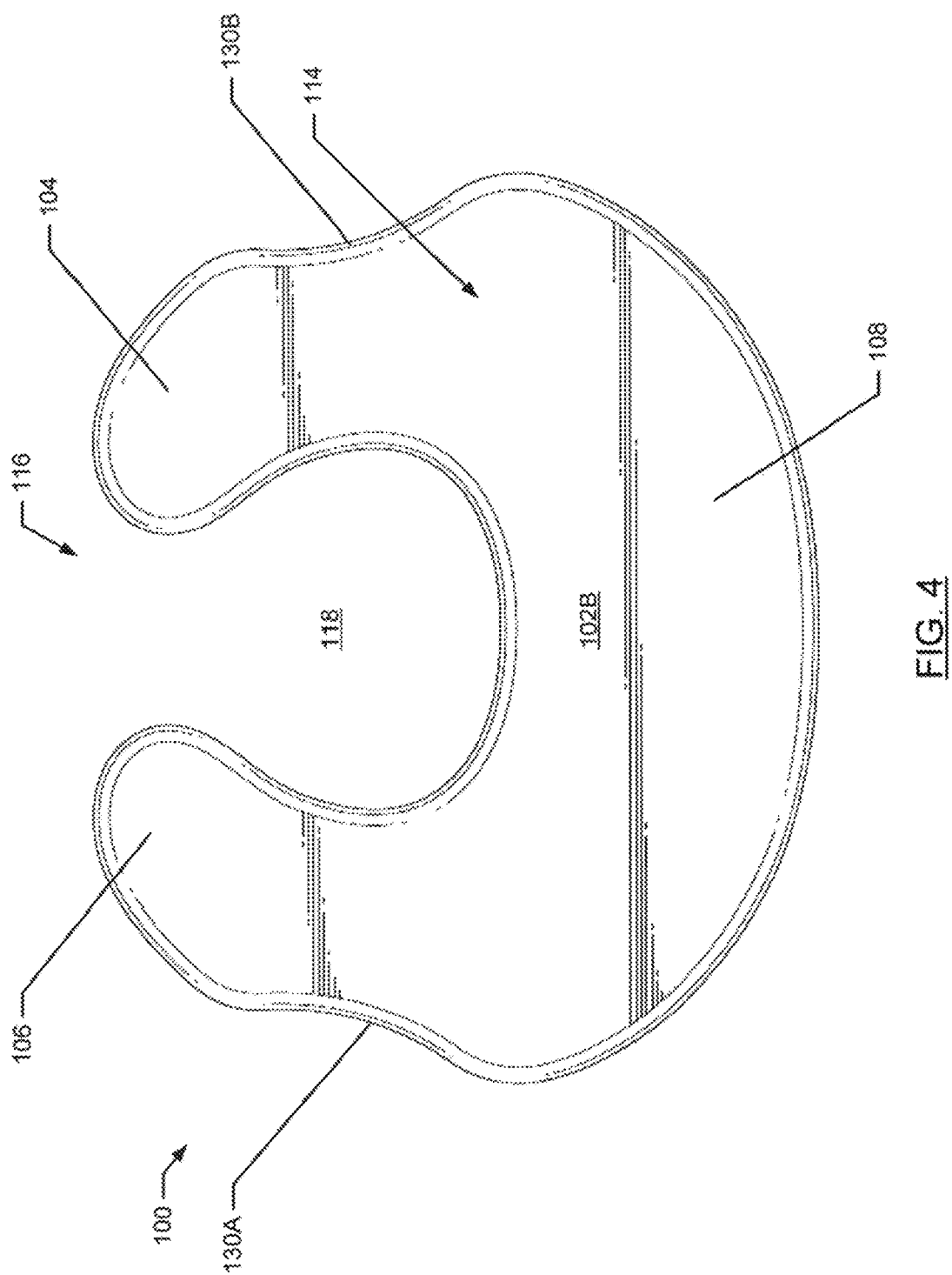
Figure 5:
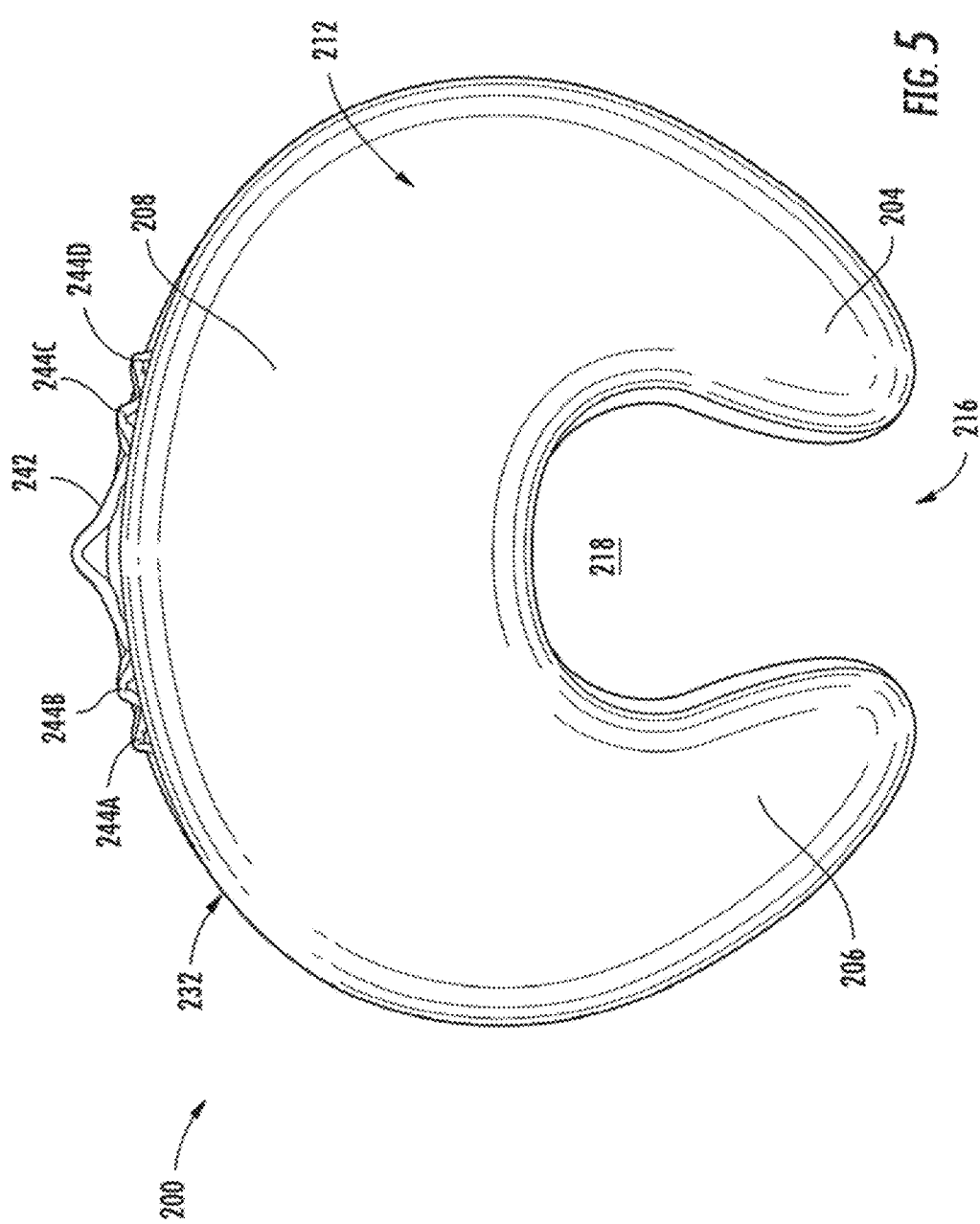
Figure 6:
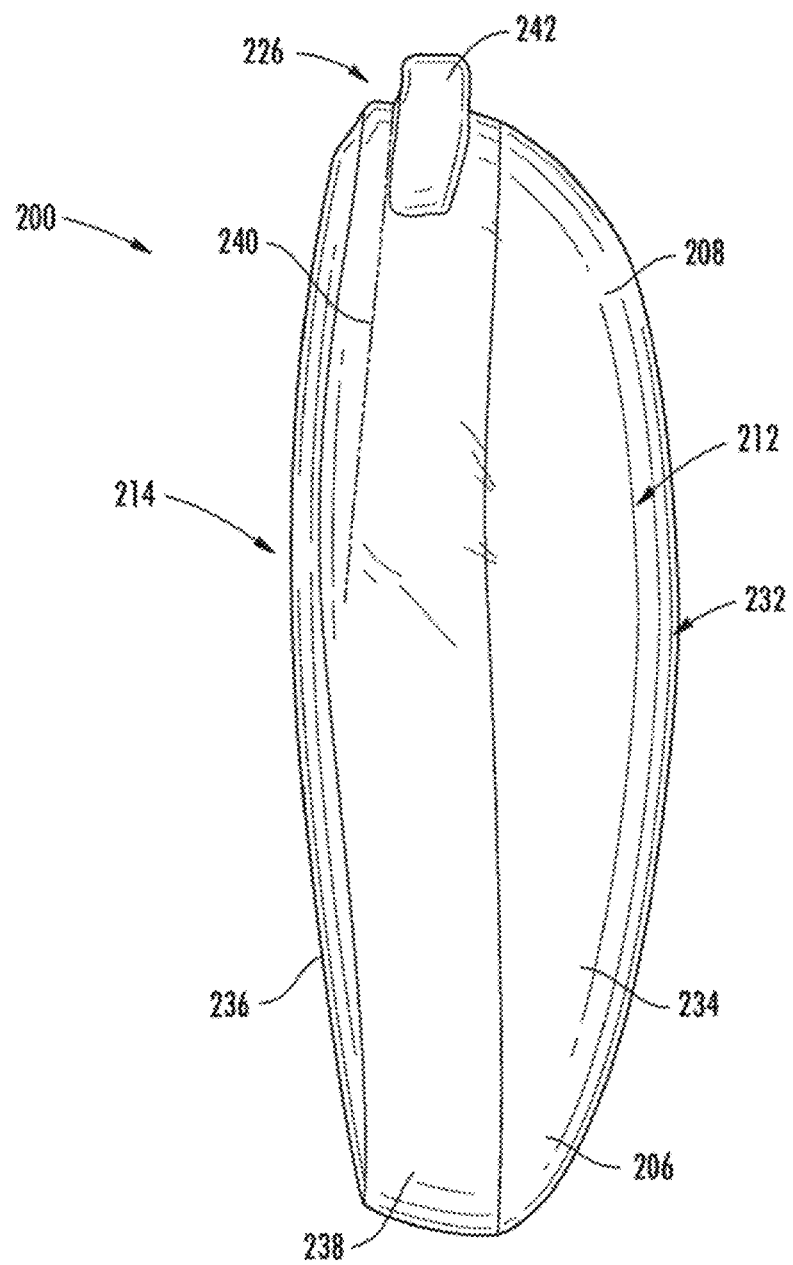
Figure 7:
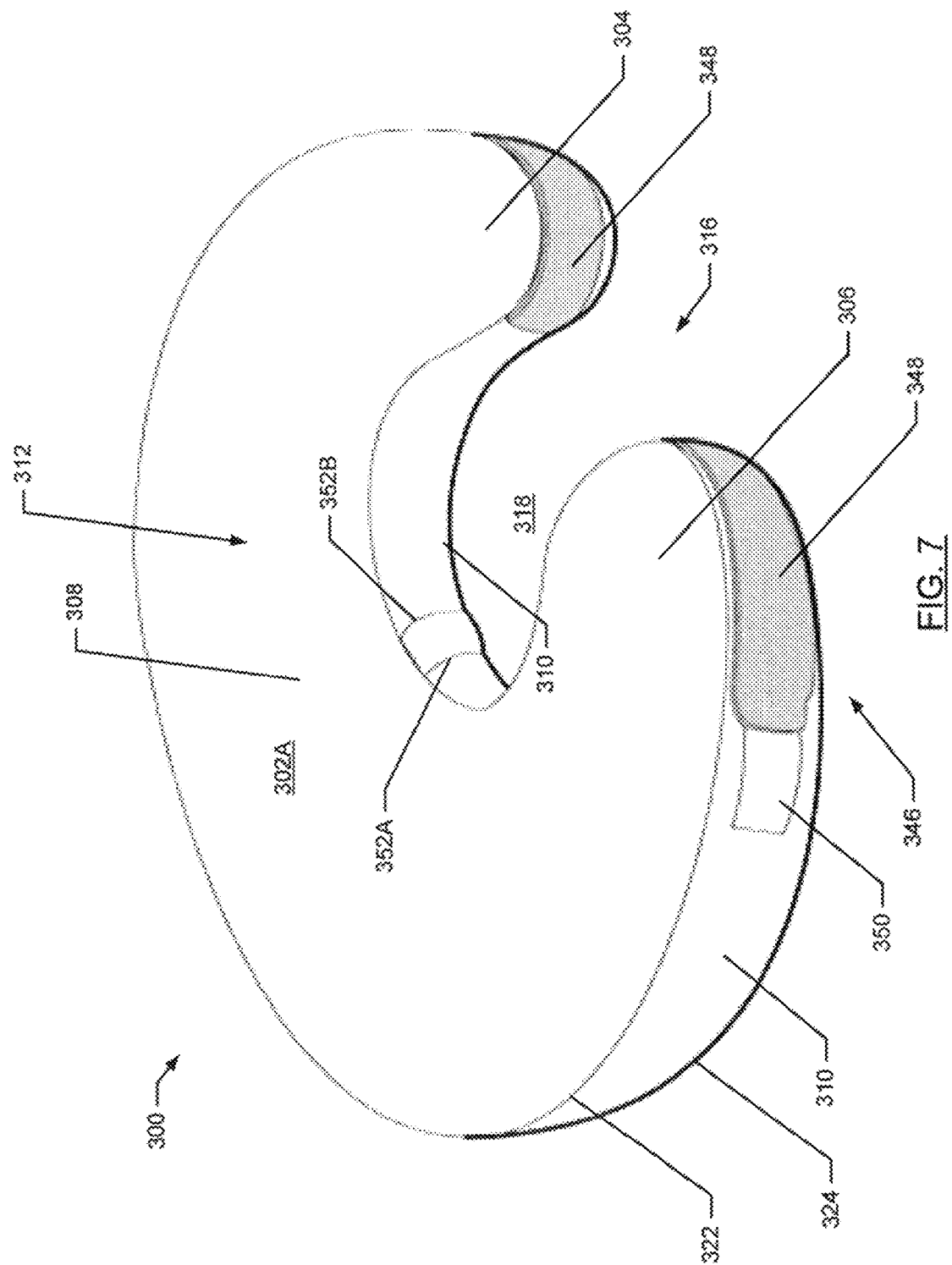
Figure 8:
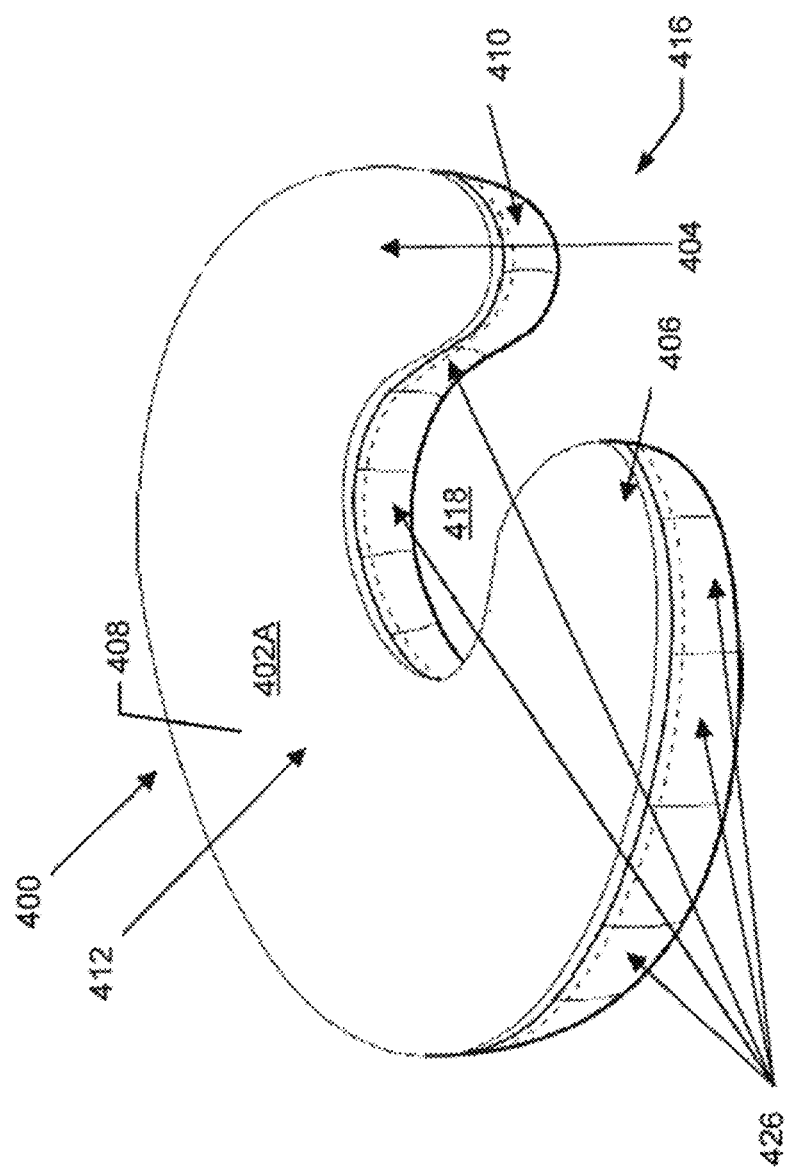
Figure 9:
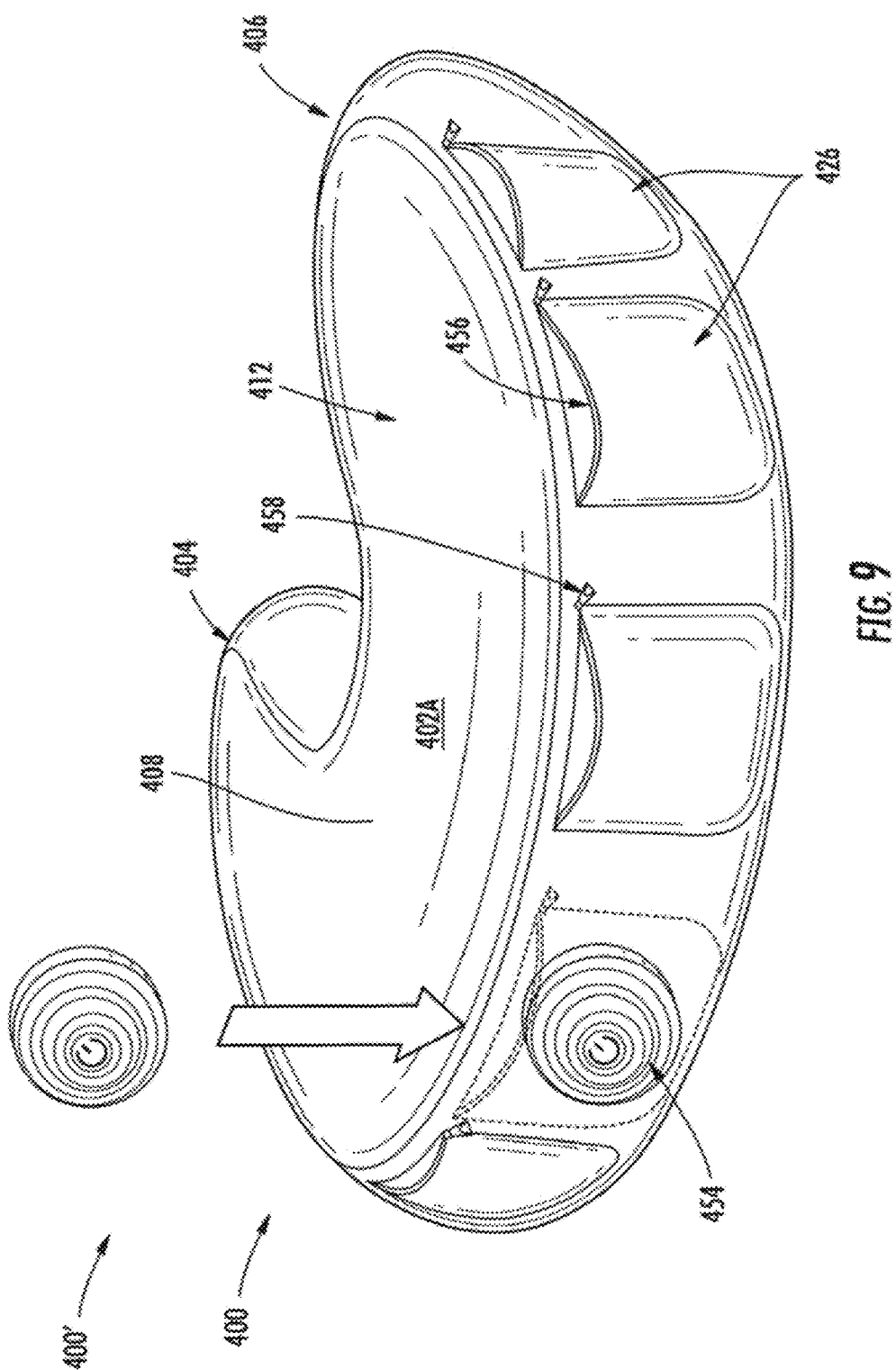
Figure 10:
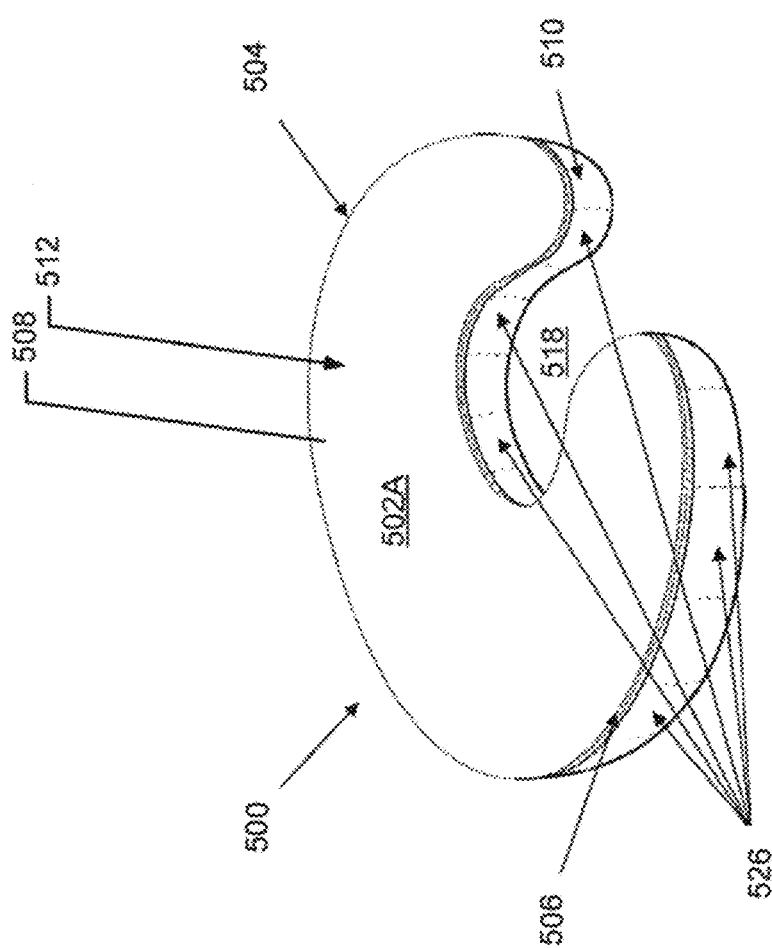
Figure 11:
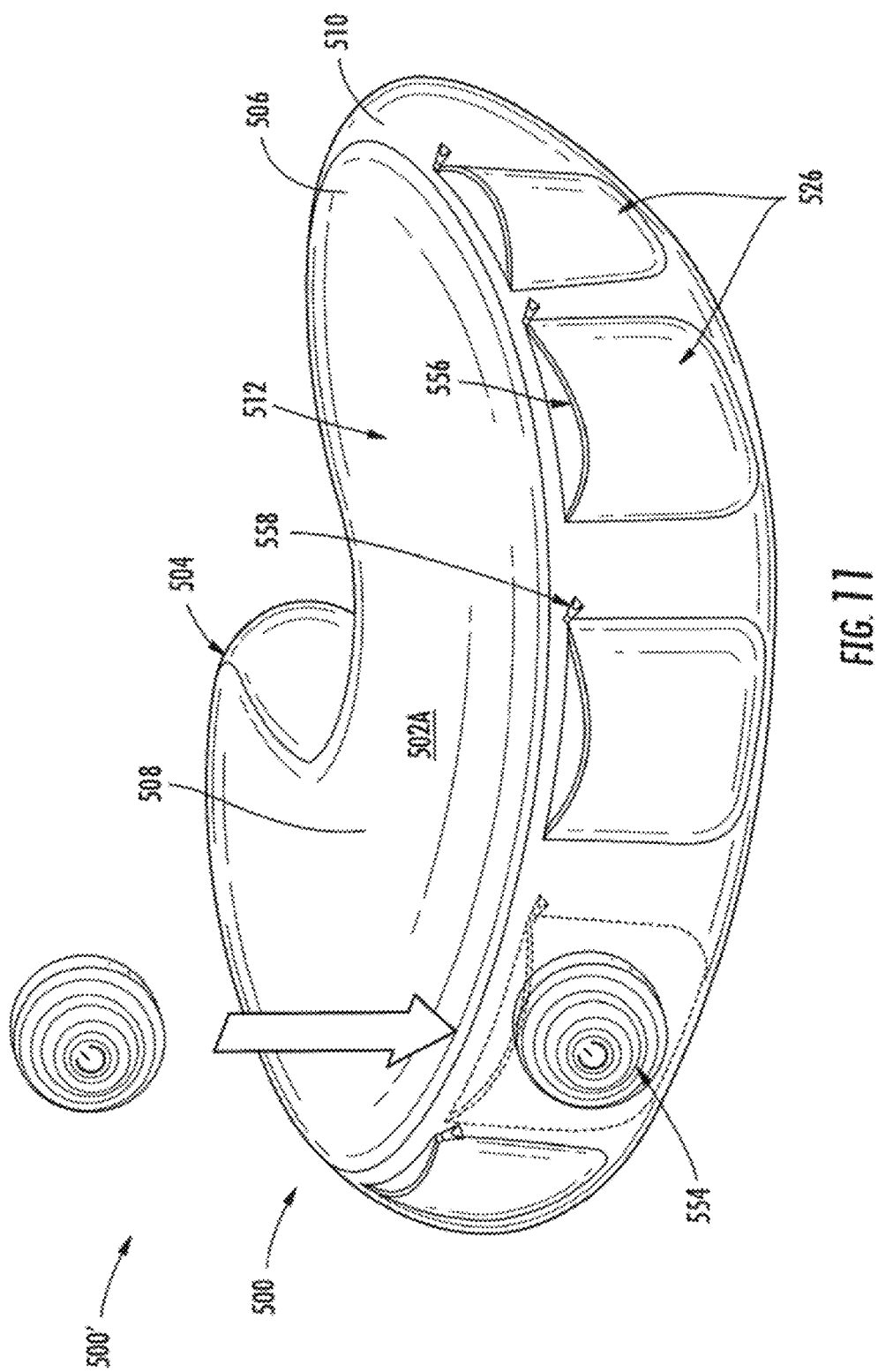
Figure 12:
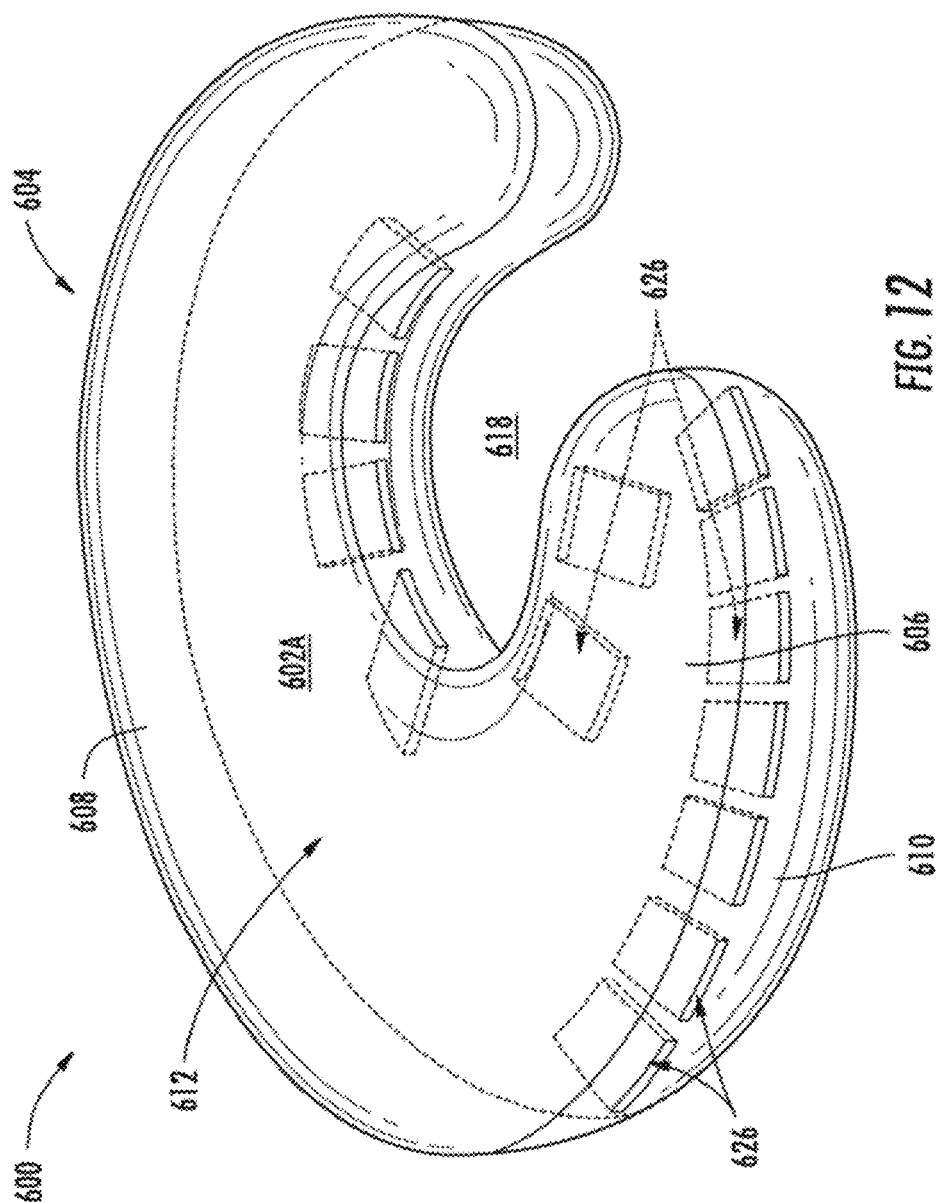
Figure 13:
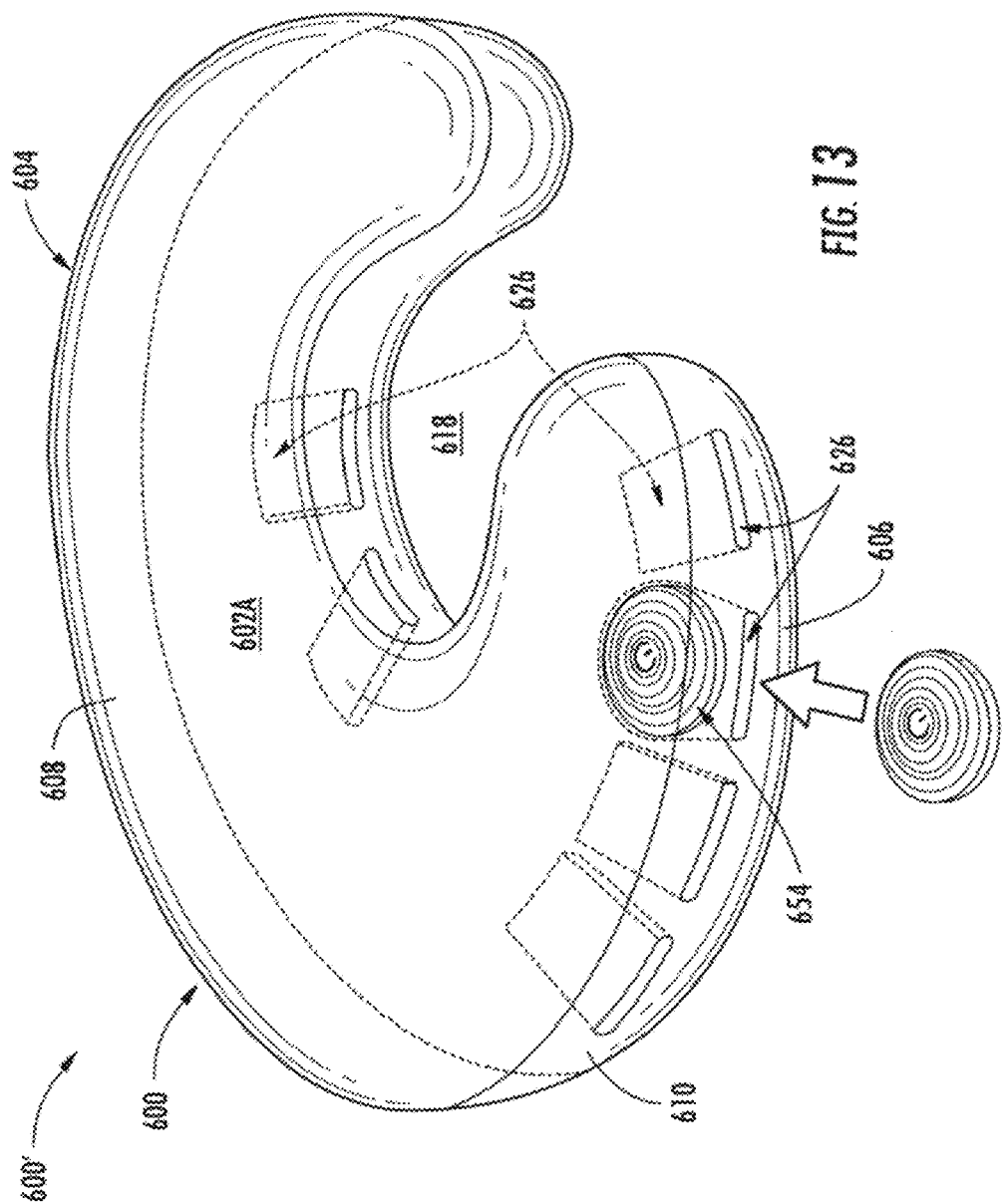
Figure 14:
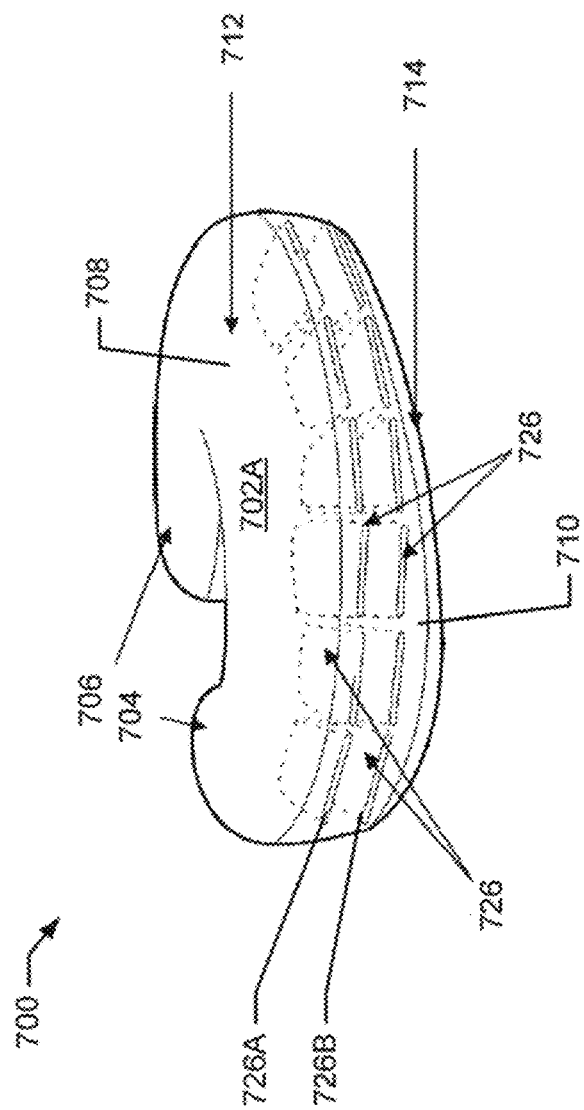
Figure 15:
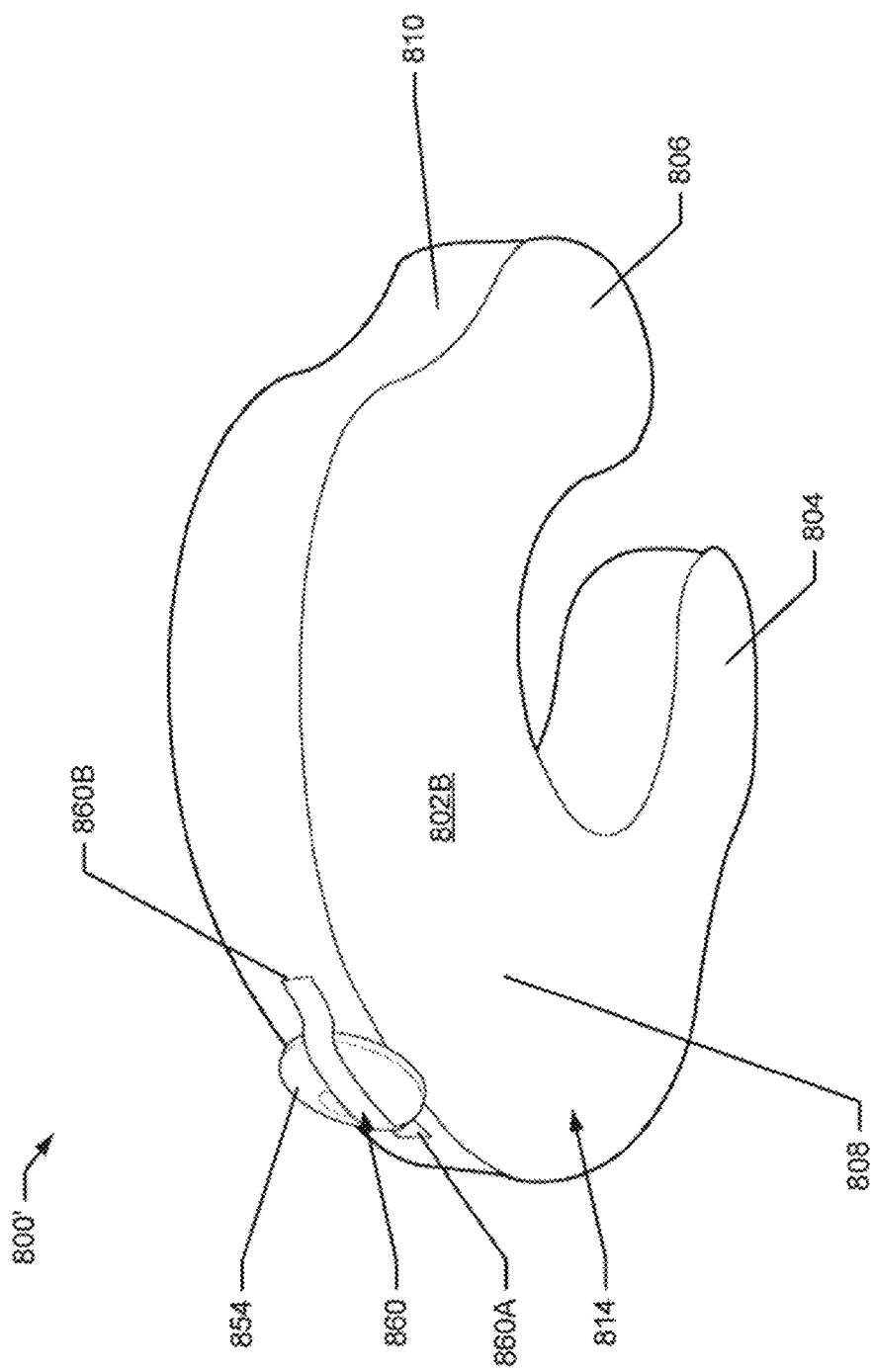
Figure 16:
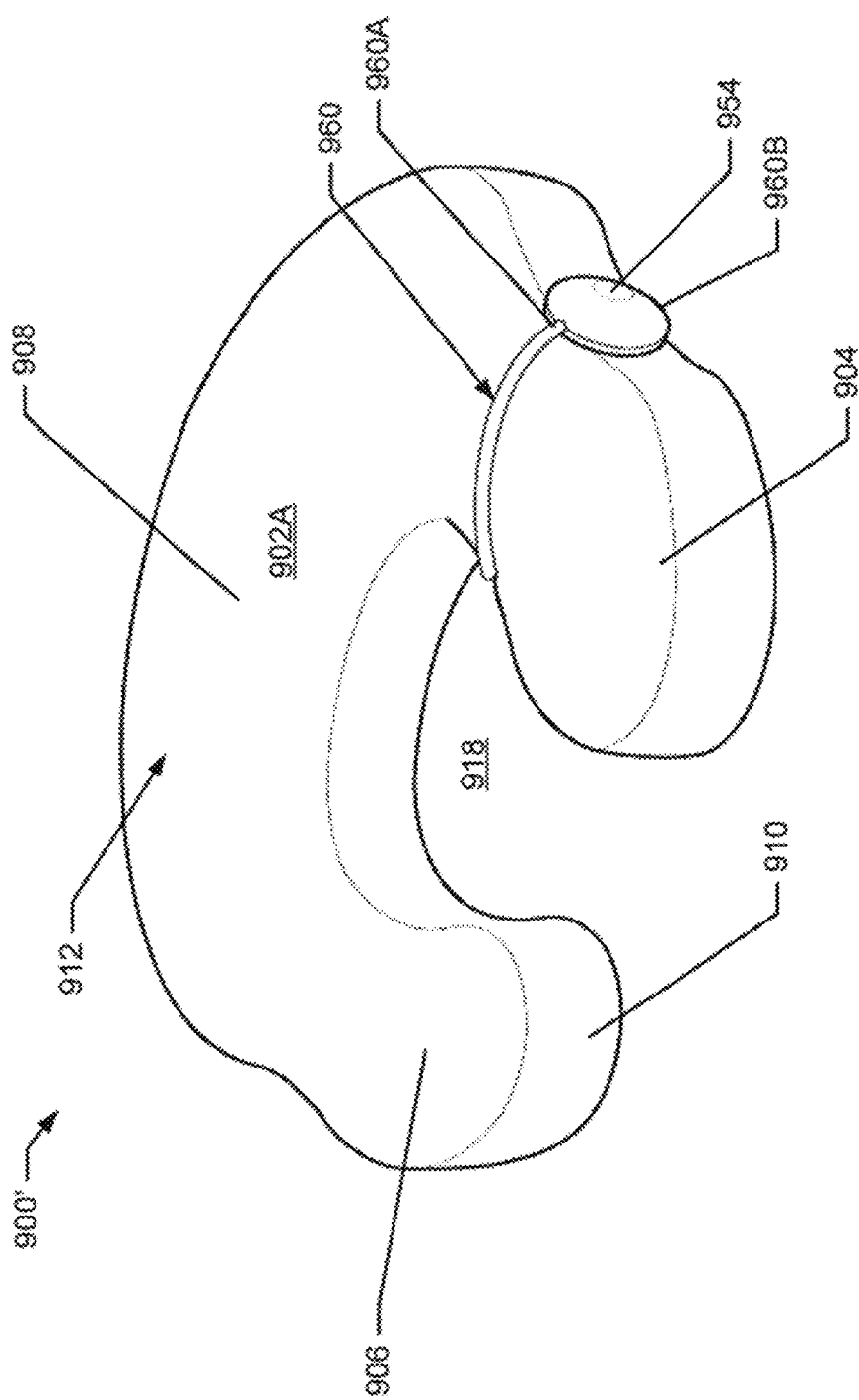
Figure 17:
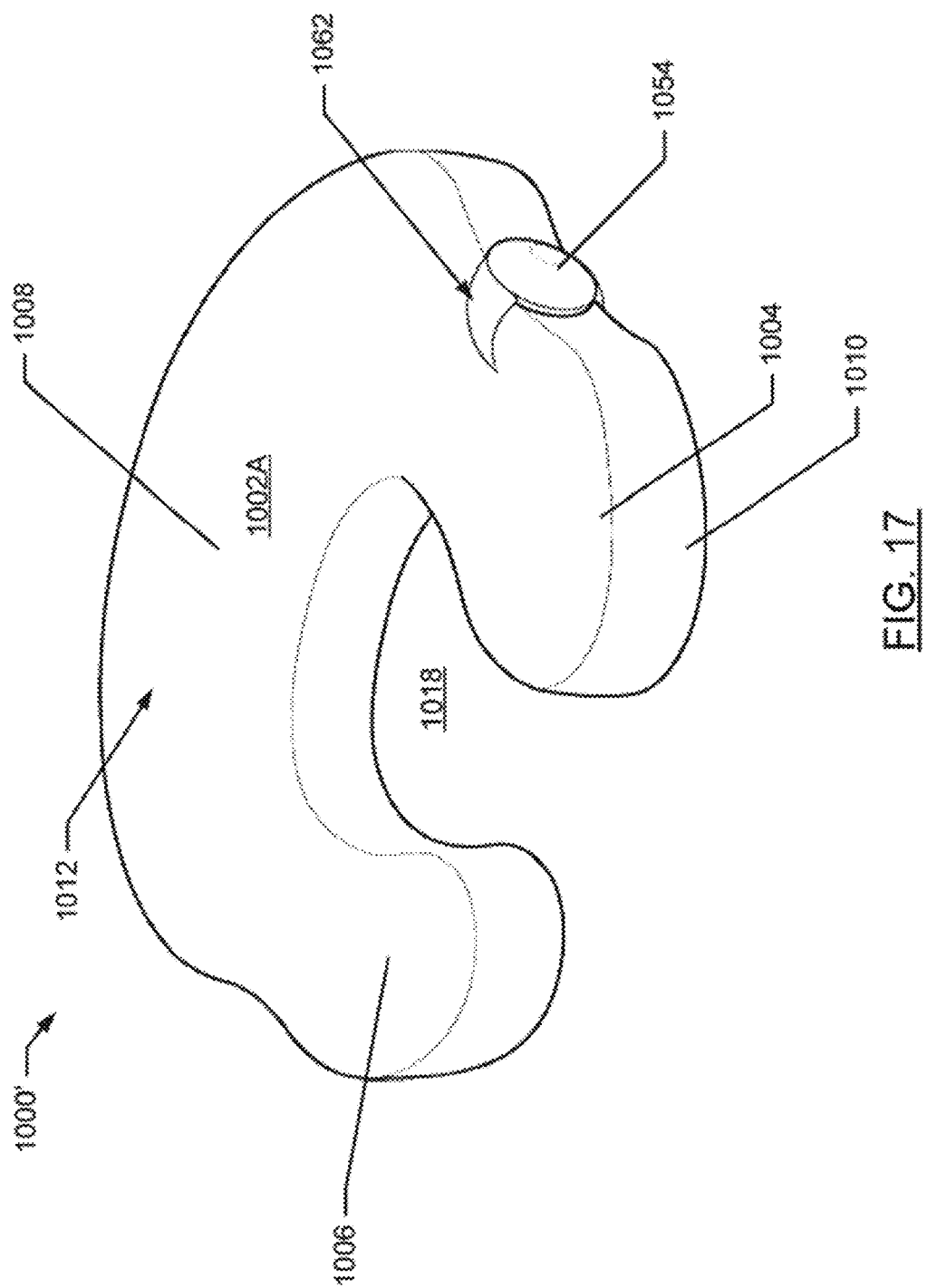
Figure 18:
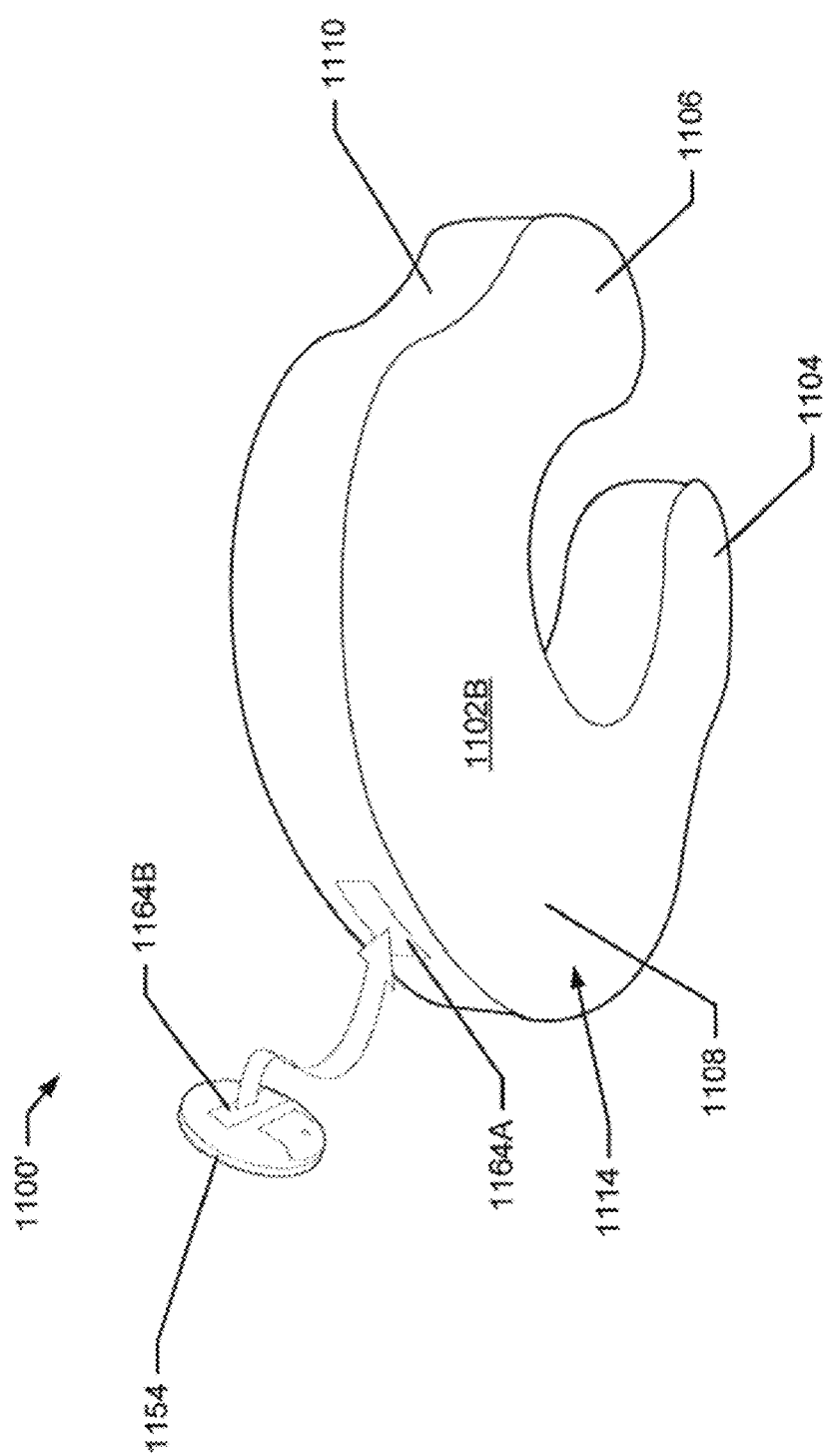
Figure 19:
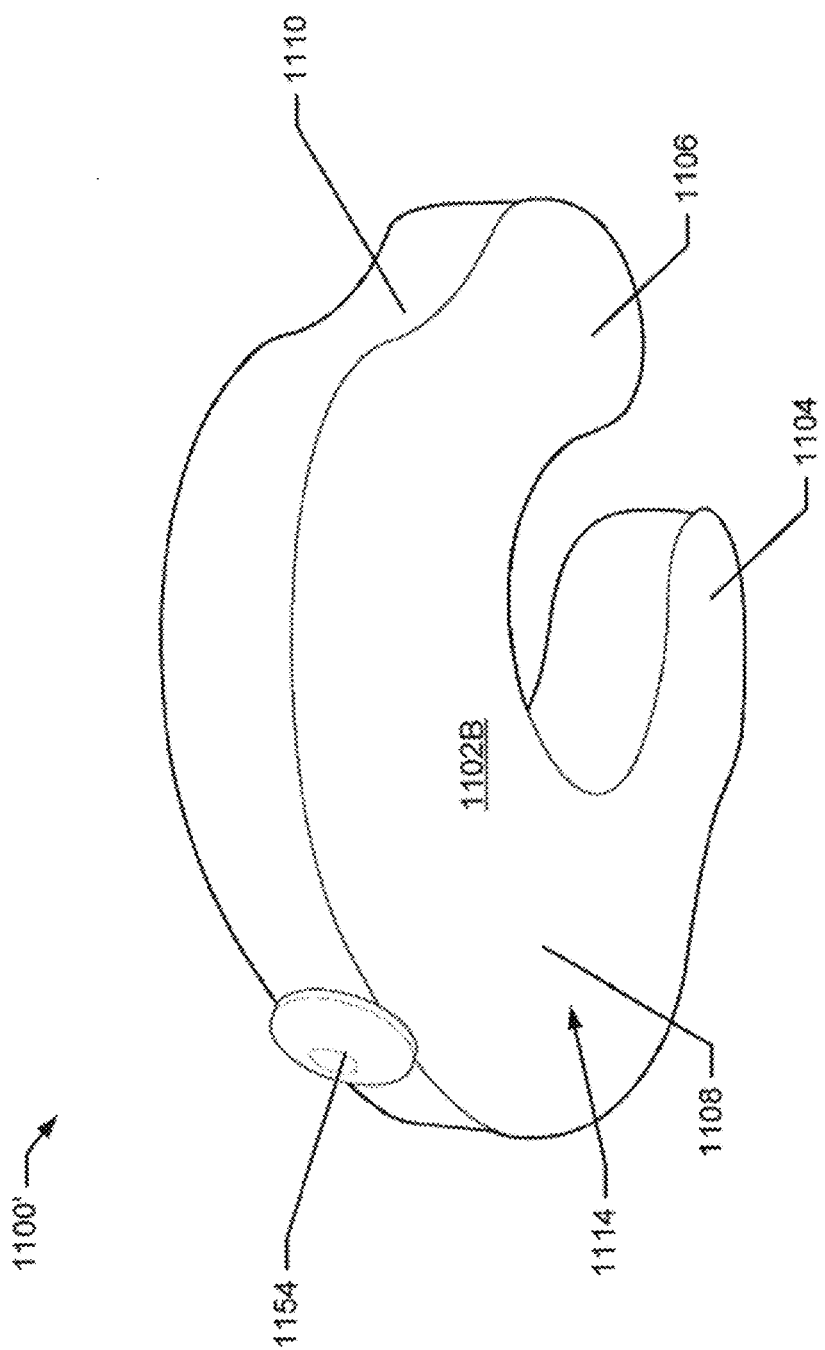
Figure 20:
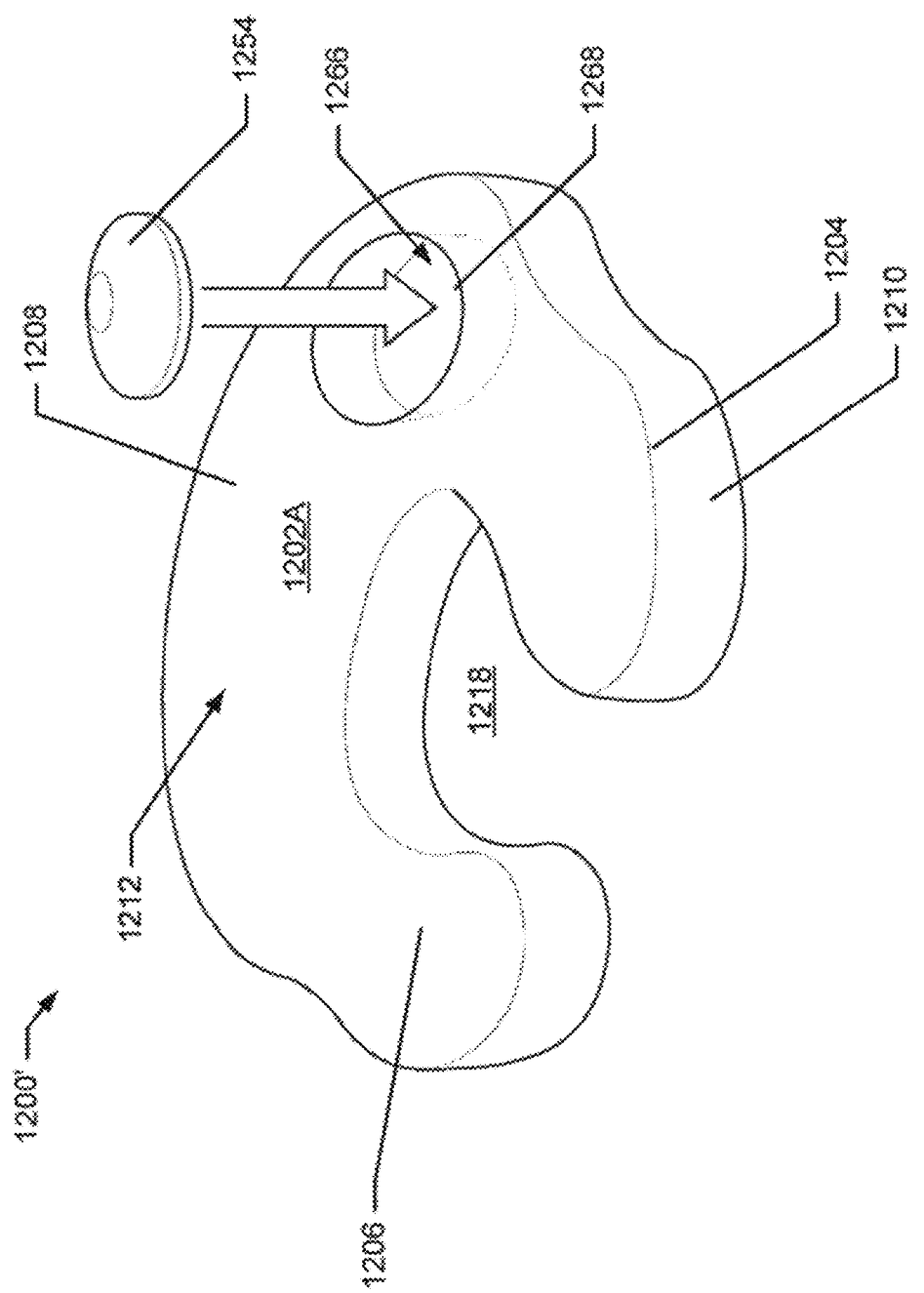
Figure 21:
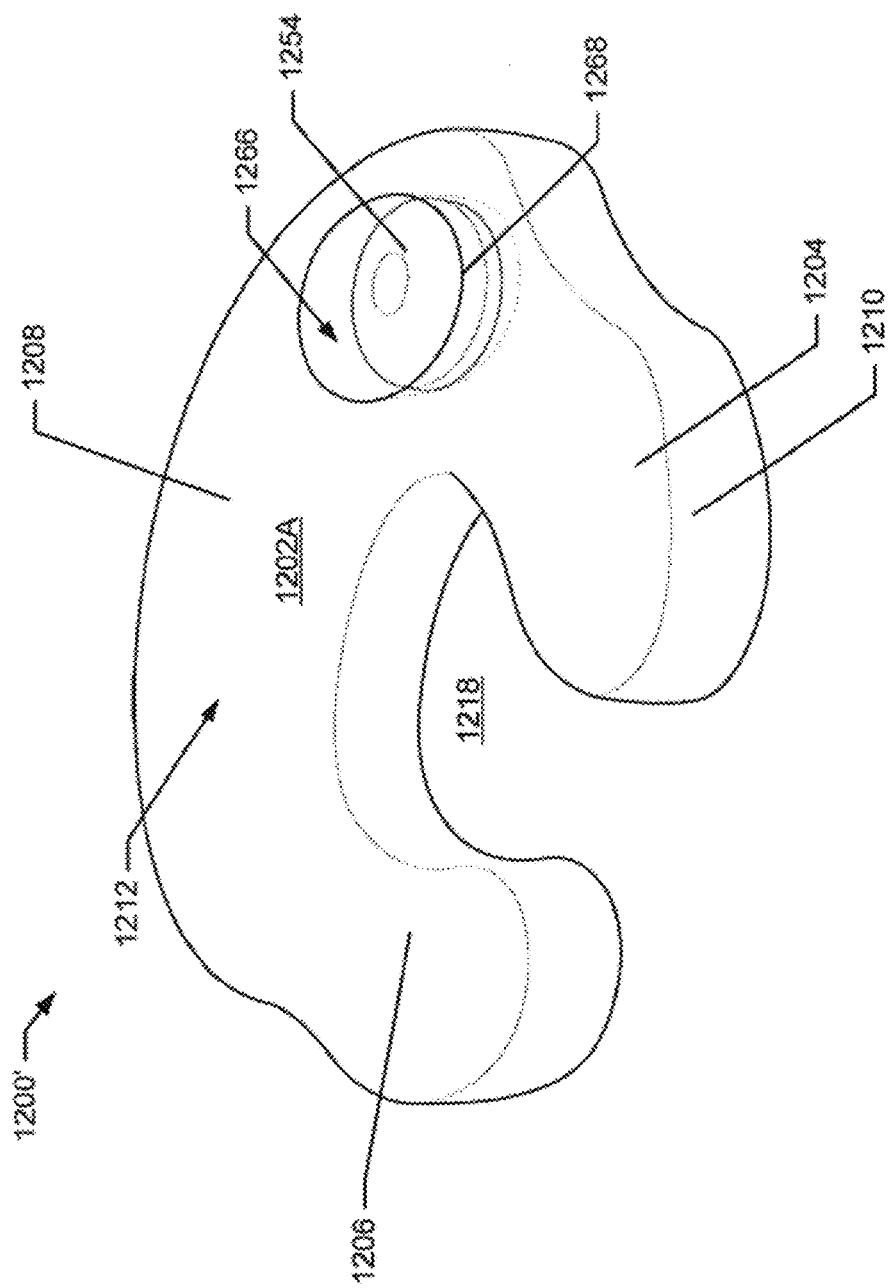
Figure 22:
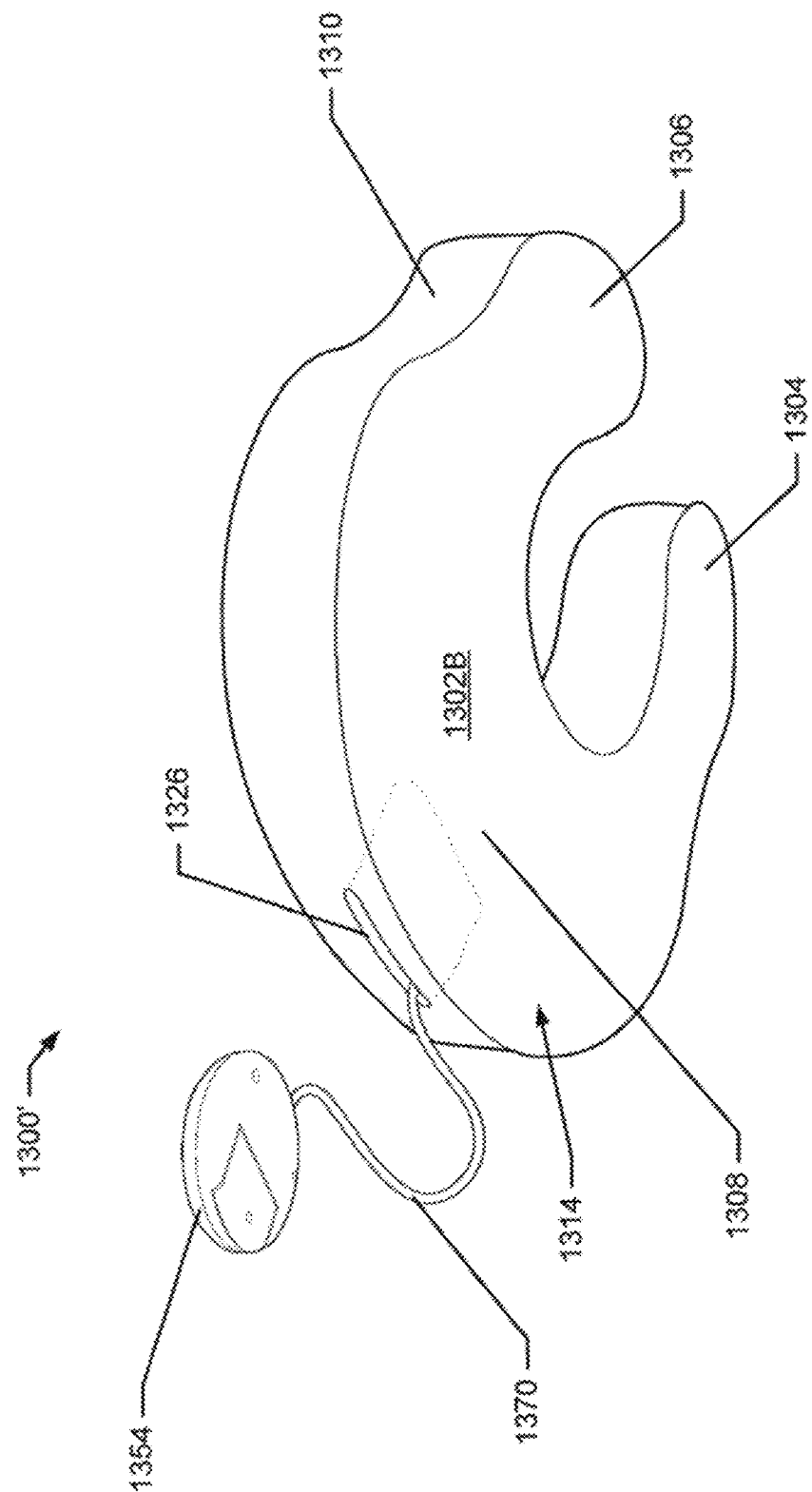
Figure 23:
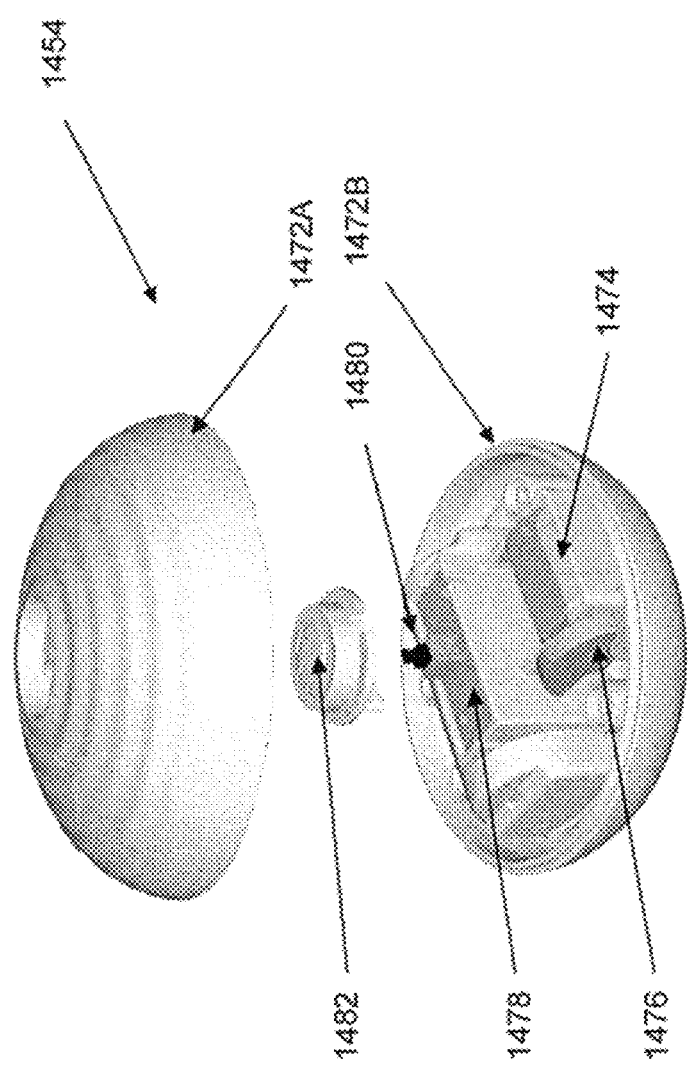
Figure 24:
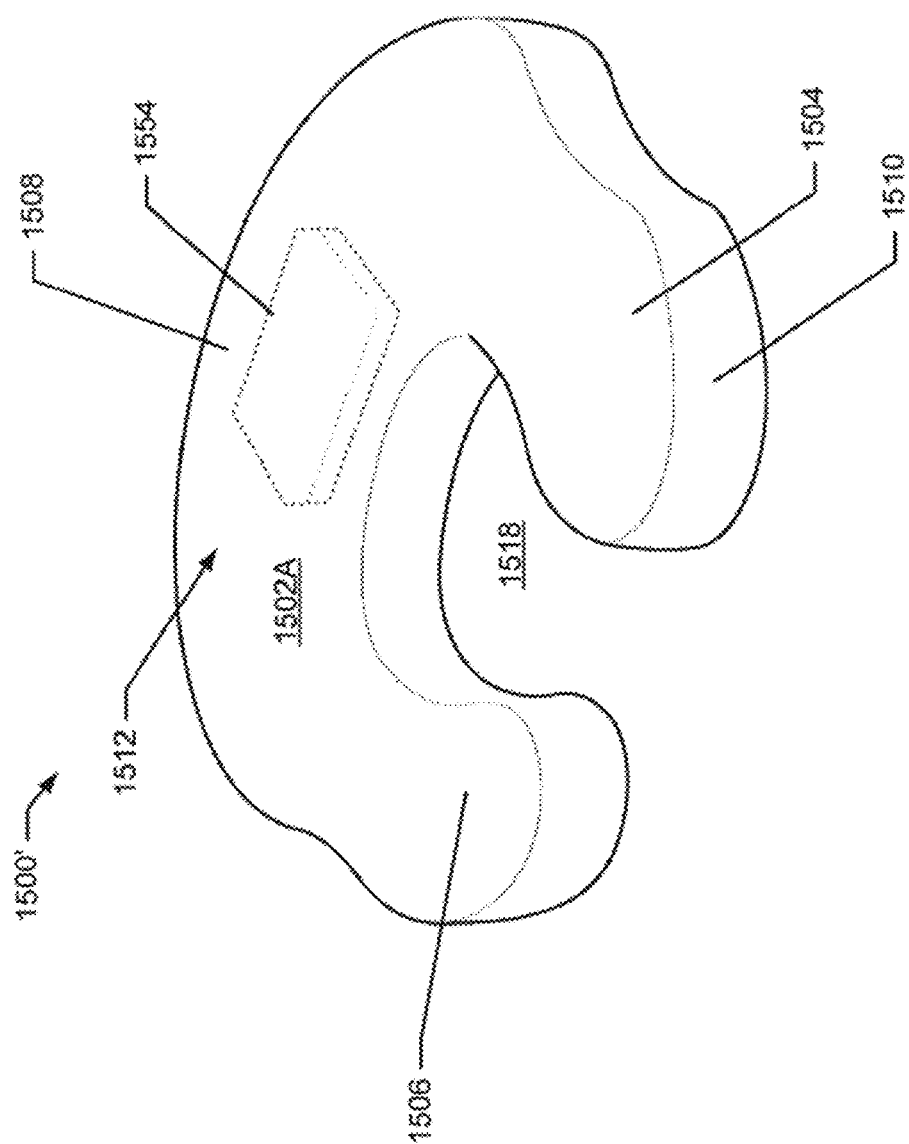
Figure 25:
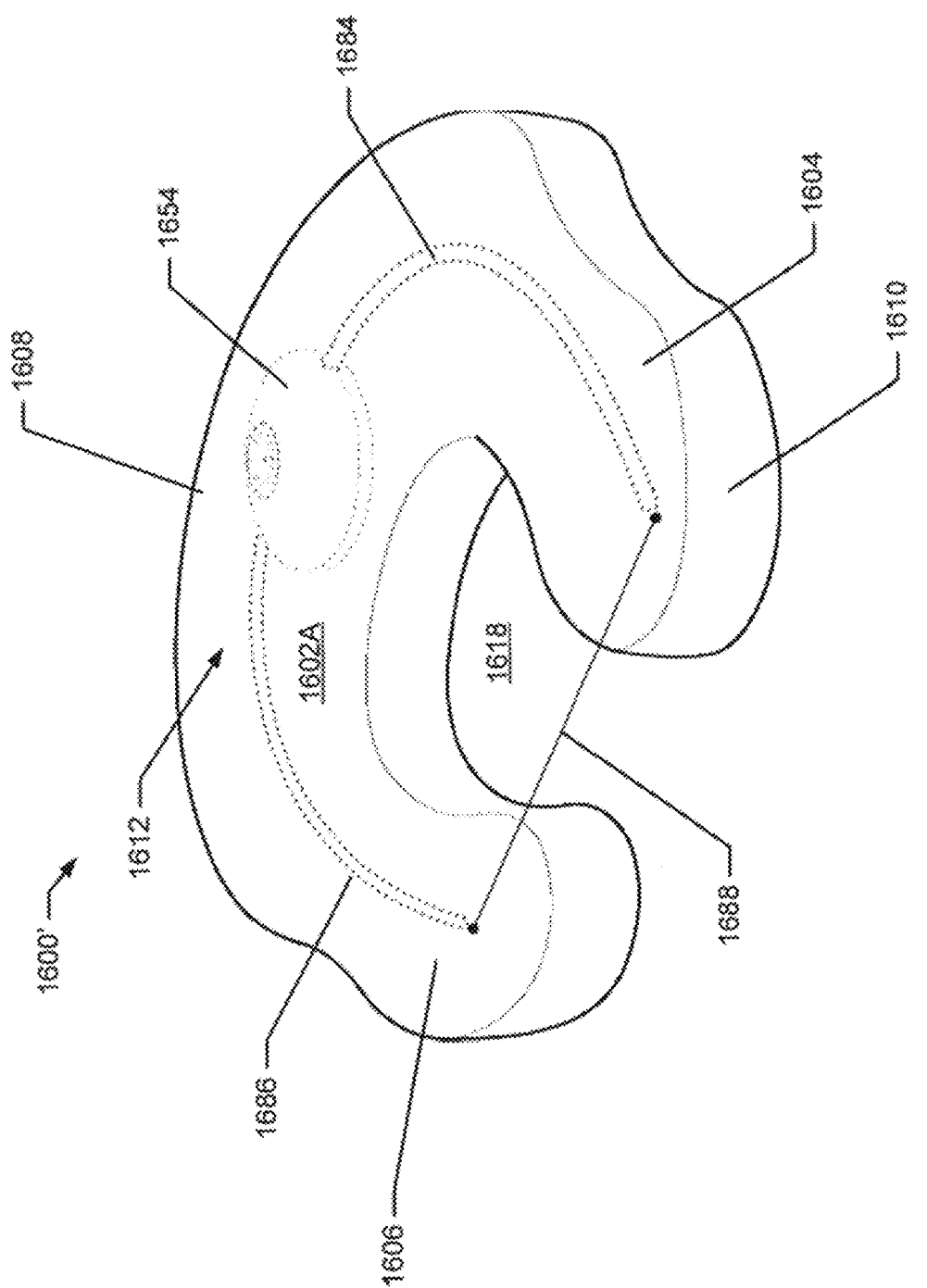
Figure 26:
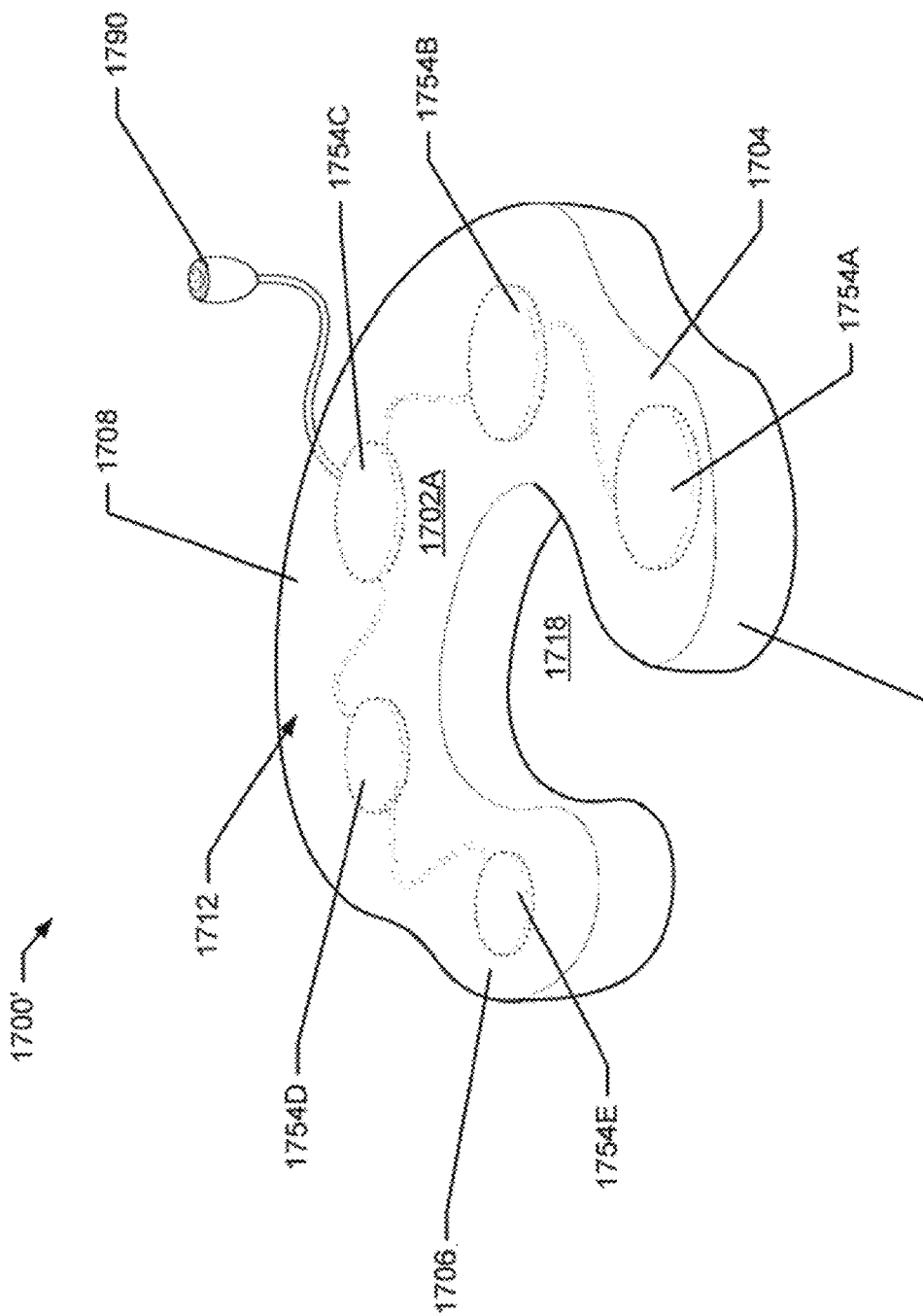
Figure 27:
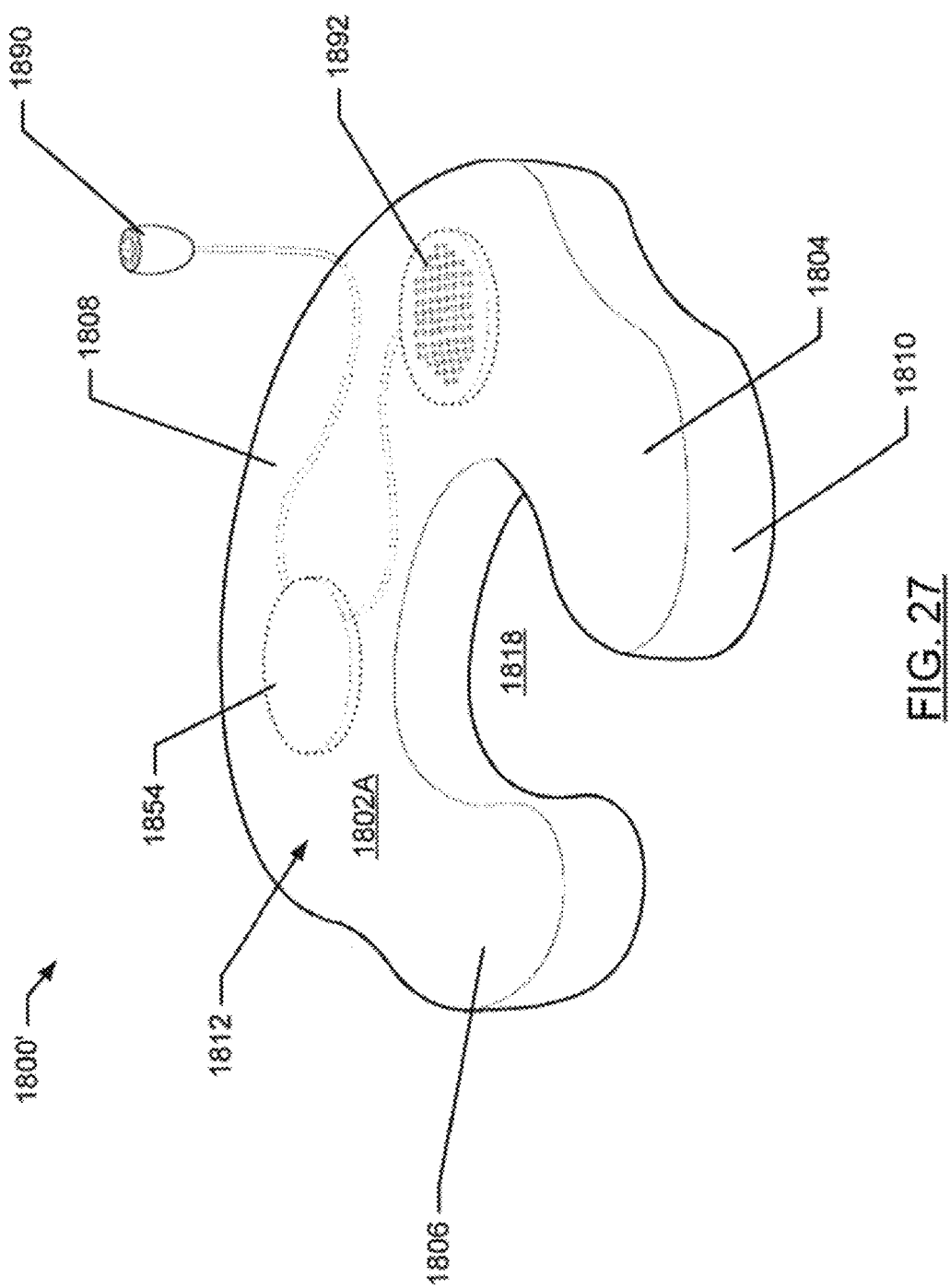
Figure 28:
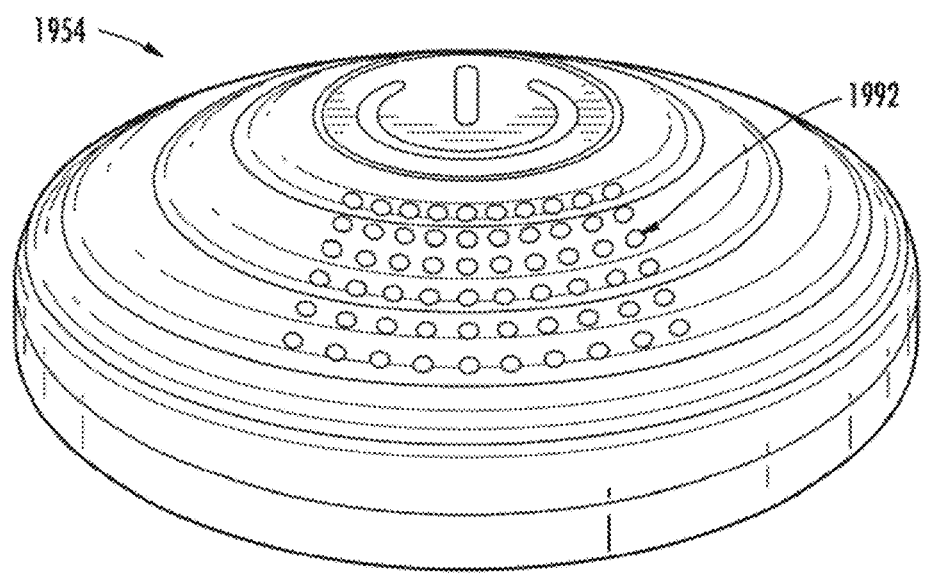
Figure 29:
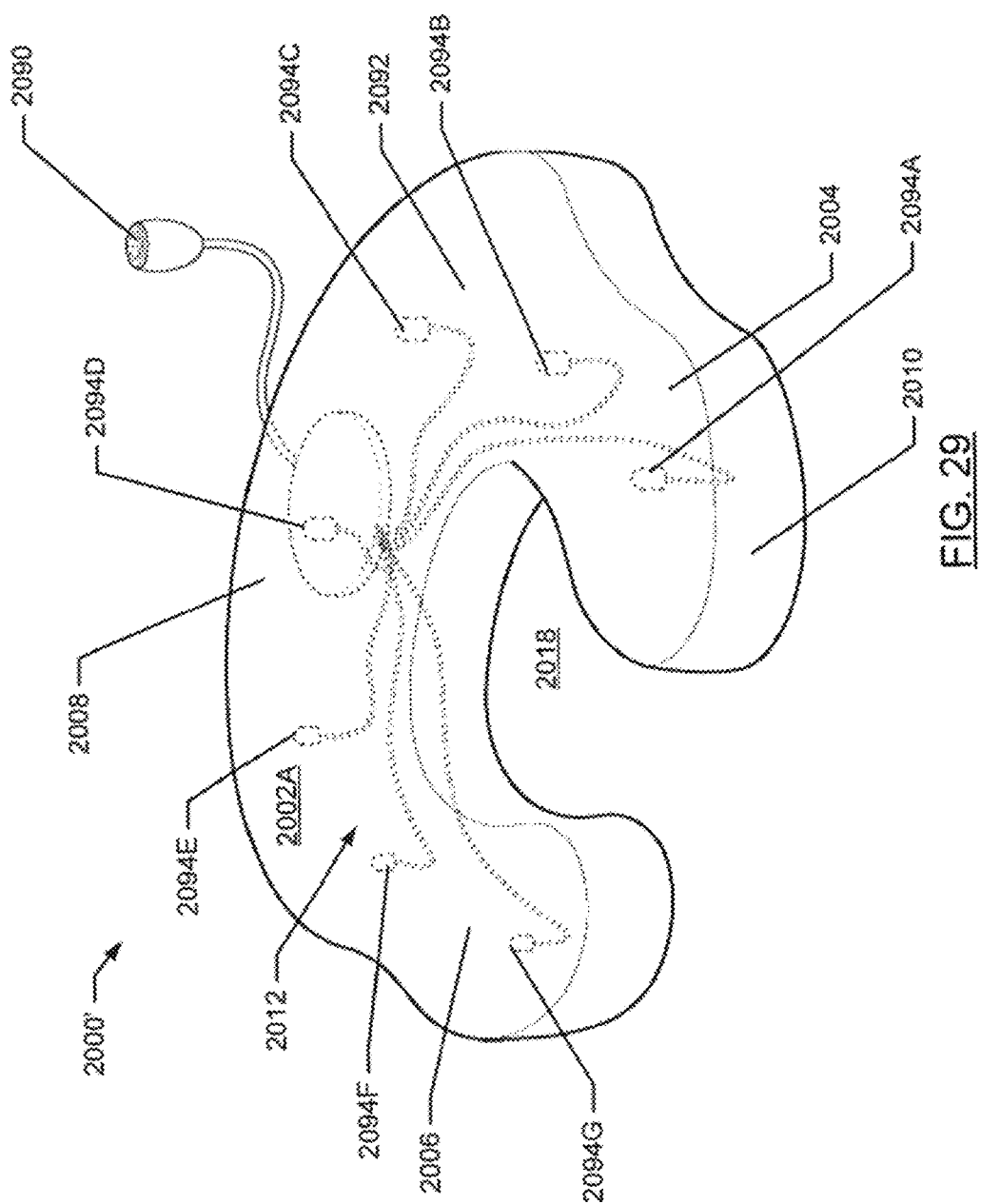
Figure 30:
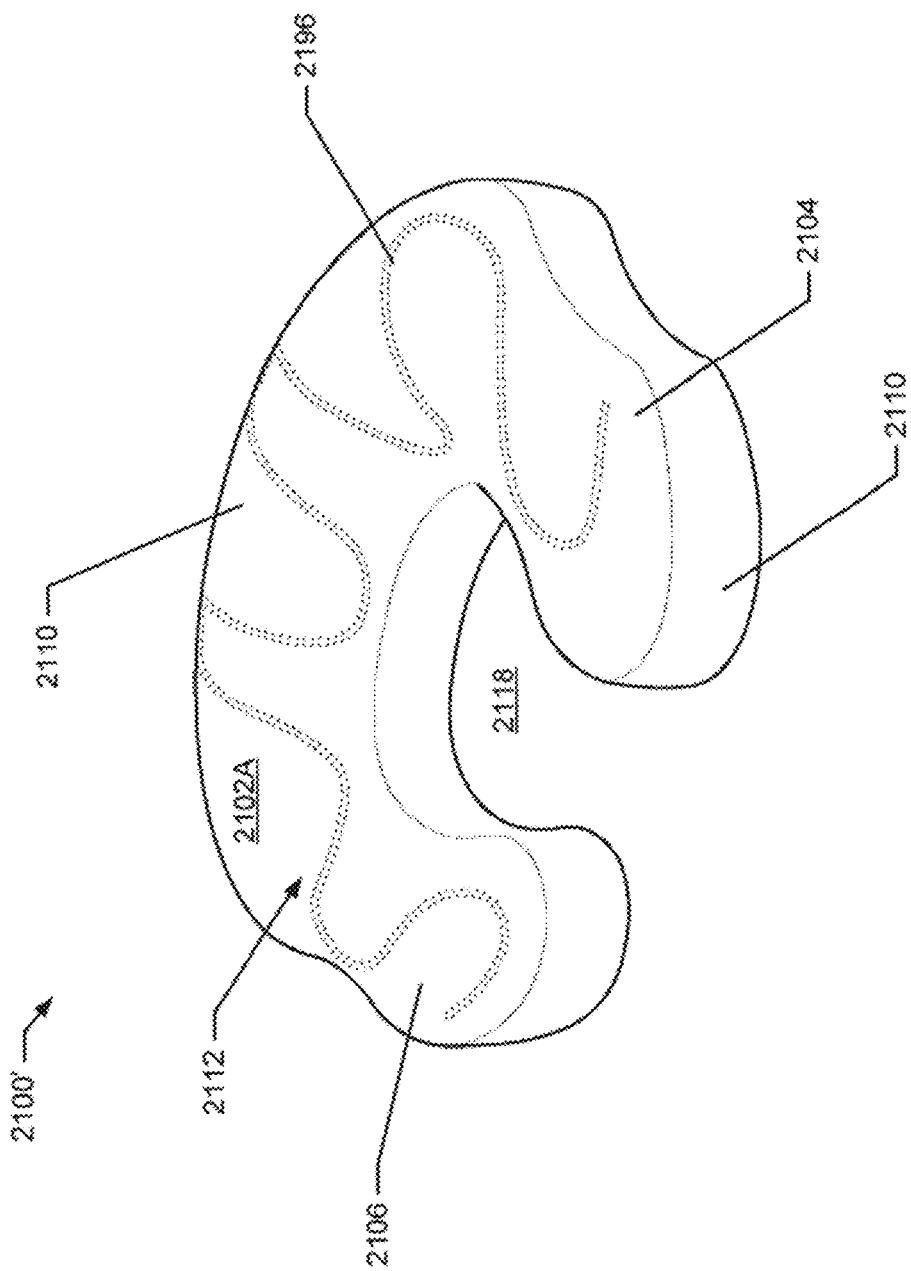
Figure 31:
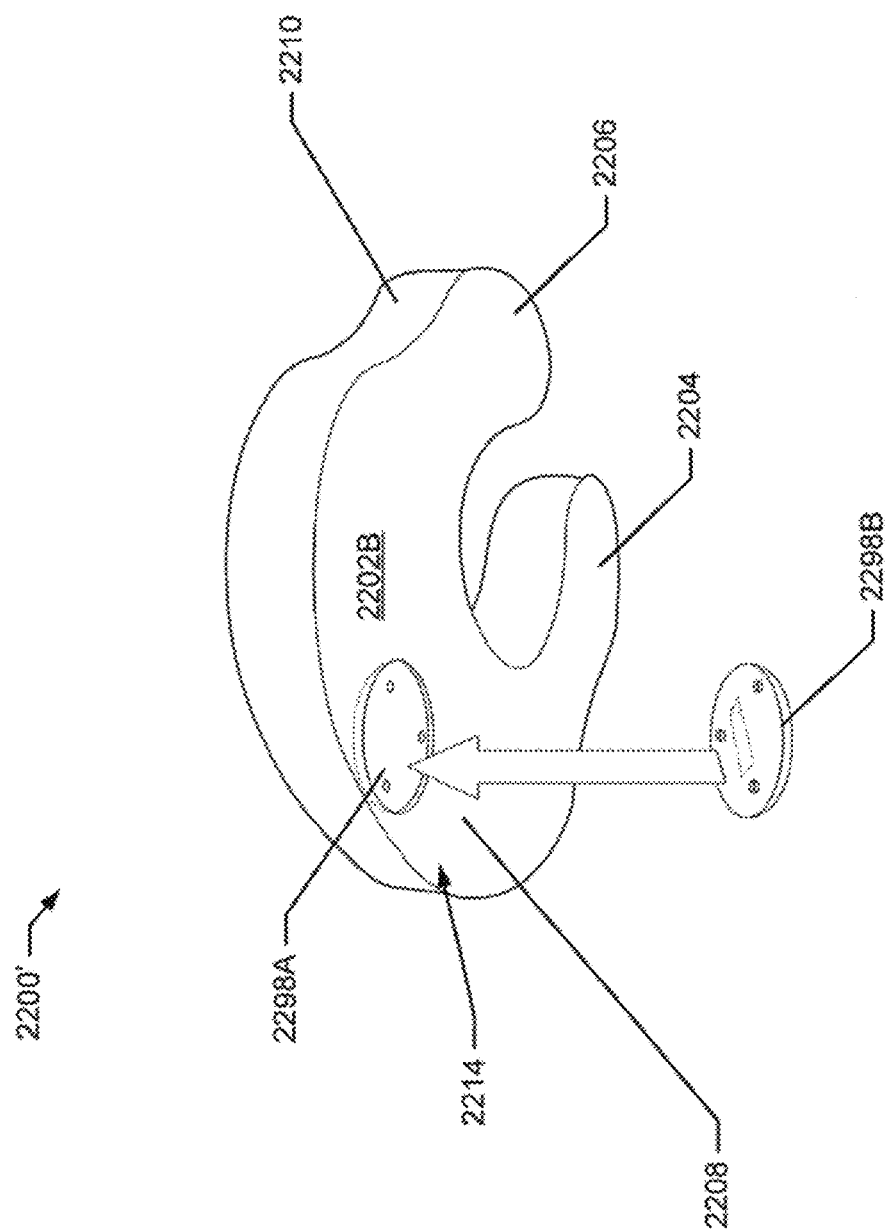
Figure 32:
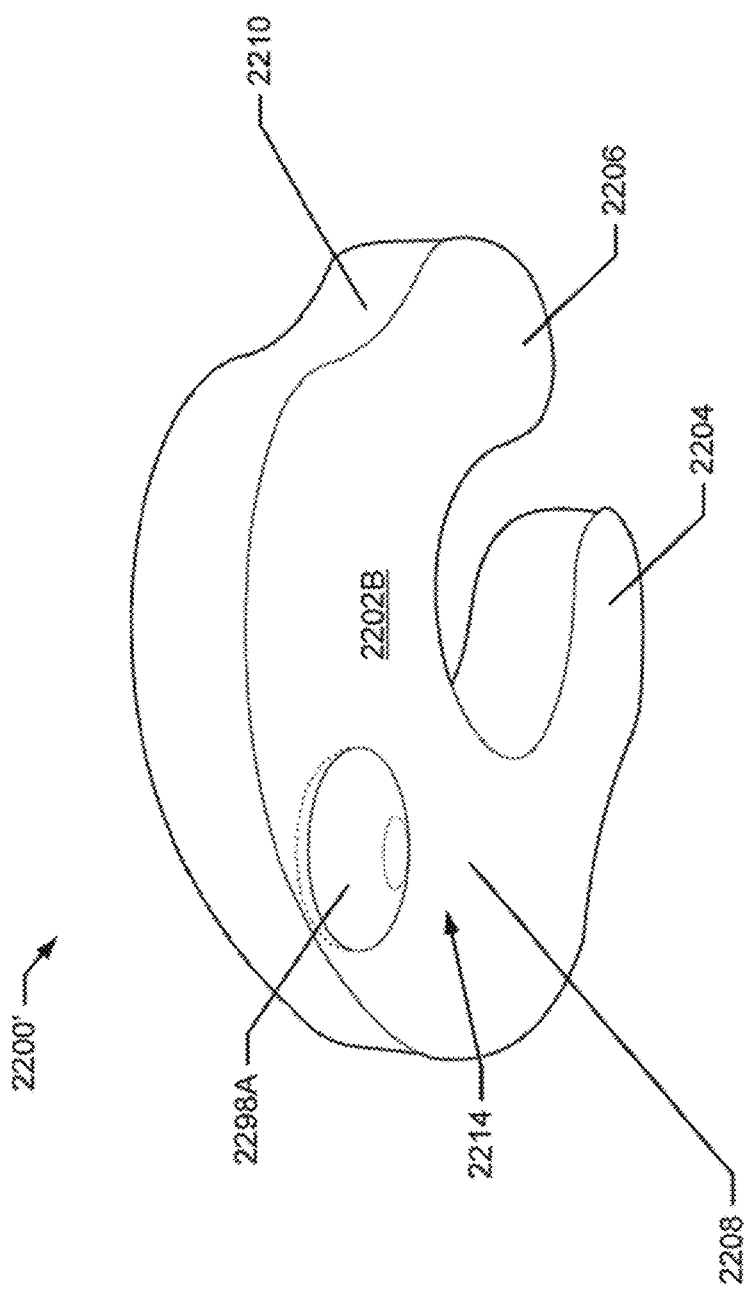
Figure 33:
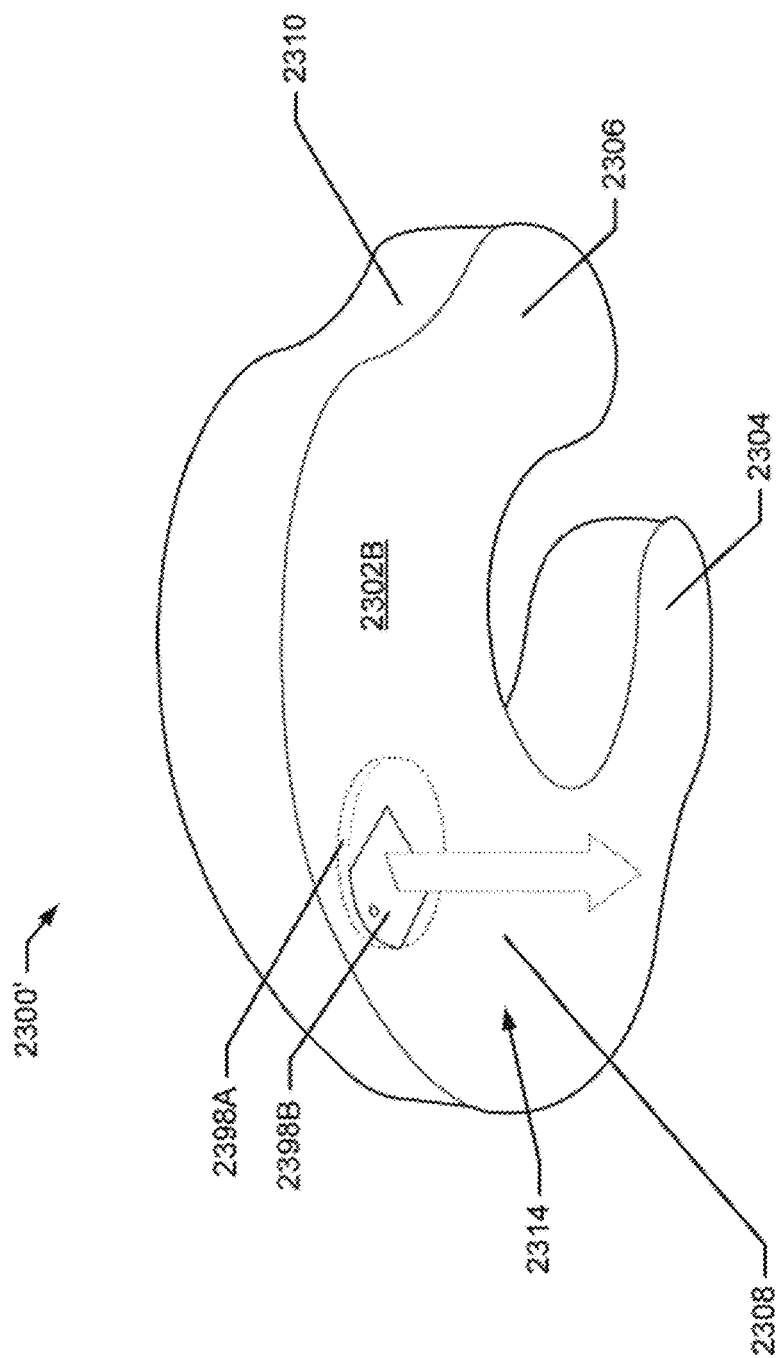
Figure 34:
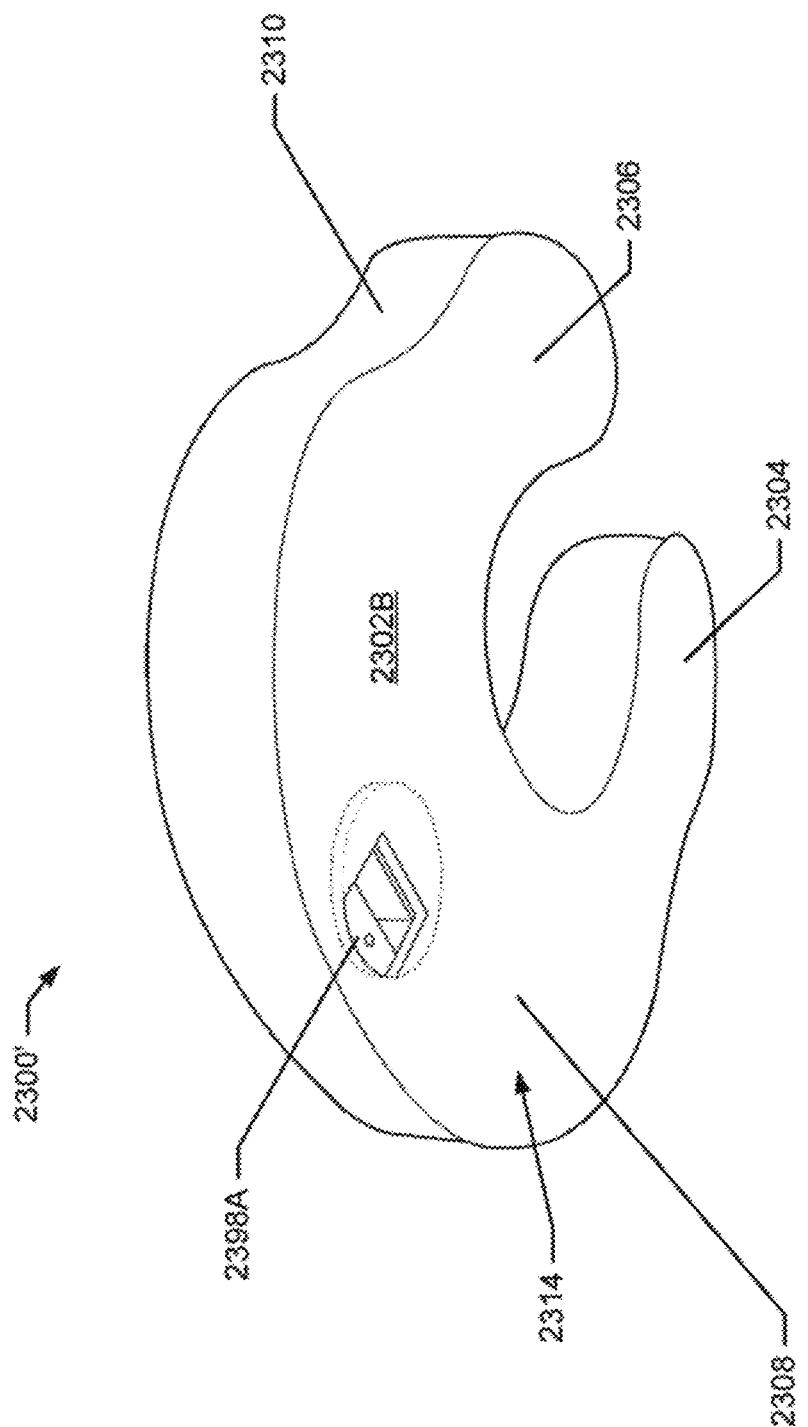

Having thus described the disclosure in general terms, reference will now be made to the accompanying figures, which are not necessarily drawn to scale, and wherein:

FIG. 1 illustrates a perspective view of a support pillow according to a first example embodiment;

FIG. 2 illustrates a front view of the support pillow of FIG. 1;

FIG. 3 illustrates a back view of the support pillow of FIG. 1;

FIG. 4 illustrates a bottom view of the support pillow of FIG. 1;

FIG. 5 illustrates a top view of a support pillow including a cover according to a second example embodiment;

FIG. 6 illustrates a side view of the support pillow of FIG. 5;

FIG. 7 illustrates a perspective view of a support pillow including an adjustment mechanism according to a third example embodiment;

FIG. 8 illustrates a support pillow comprising external pockets according to an example embodiment;

FIG. 9 illustrates a support pillow assembly comprising the support pillow of FIG. 8 according to an example embodiment;

FIG. 10 illustrates a support pillow comprising vertically-extending internal pockets according to an example embodiment;

FIG. 11 illustrates a support pillow assembly comprising the support pillow of FIG. 10 according to an example embodiment;

FIG. 12 illustrates a support pillow comprising laterally-extending internal pockets according to an example embodiment;

FIG. 13 illustrates a support pillow assembly comprising the support pillow of FIG. 12 according to an example embodiment;

FIG. 14 illustrates a support pillow comprising laterally-extending internal pockets at differing heights according to an example embodiment;

FIG. 15 illustrates a support pillow assembly comprising a strap fixed to a support pillow according to an example embodiment;

FIG. 16 illustrates a support pillow assembly comprising a strap fixed to an accessory device according to an example embodiment;

FIG. 17 illustrates a support pillow assembly comprising a clip according to an example embodiment;

FIG. 18 illustrates a support pillow assembly comprising cooperating hook and loop fasteners in an unattached configuration according to an example embodiment;

FIG. 19 illustrates the support pillow assembly of FIG. 18 in an attached configuration;

FIG. 20 illustrates a support pillow assembly comprising a cavity according to an example embodiment;

FIG. 21 illustrates the support pillow assembly of FIG. 20 when an accessory device is positioned in the cavity;

FIG. 22 illustrates a support pillow assembly comprising a tether according to an example embodiment;

FIG. 23 illustrates an exploded view of a curved vibration unit according to an example embodiment;

FIG. 24 illustrates a support pillow assembly comprising a rectangular vibration unit according to an example embodiment;

FIG. 25 illustrates a support pillow assembly comprising a vibration unit with a vibration transmitter according to an example embodiment;

FIG. 26 illustrates a support pillow assembly comprising a plurality of interconnected vibration units according to an example embodiment;

FIG. 27 illustrates a support pillow assembly comprising a vibration unit and a separate speaker according to an example embodiment;

FIG. 28 illustrates a support pillow assembly comprising an integral vibration unit and speaker according to an example embodiment;

FIG. 29 illustrates a support pillow assembly comprising a plurality of illumination elements according to an example embodiment;

FIG. 30 illustrates a support pillow assembly comprising a thermal element according to an example embodiment;

FIG. 31 illustrates a support pillow assembly comprising an accessory device comprising a removable portion that has been removed according to an example embodiment;

FIG. 32 illustrates the support pillow assembly of claim 31 when the removable portion has been attached;

FIG. 33 illustrates a support pillow assembly comprising an accessory device comprising a removable portion in the form of a battery box that is attached according to an example embodiment; and FIG. 34 illustrates the support pillow assembly of FIG. 33 when the removable portion has been removed.

DETAILED DESCRIPTION

The disclosure now will be described more fully hereinafter through reference to various embodiments. These embodiments are provided so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used herein, the singular forms "a", "an", "the", include plural referents unless the context clearly dictates otherwise.

Referring initially to FIG. 1, an embodiment of a support pillow 100 is provided. The support pillow 100 may comprise a fabric shell that may be defined by a first substantially laterally-extending panel 102A (see, e.g., FIG. 1) and a second laterally-extending panel 102B (see, e.g., FIG. 4), and collectively referred to herein as fabric shell 102. The fabric shell 102 may at least partially enclose a resilient fill material. The resilient fill material may comprise one or more layers of polyester batting, foam, loose fill material, and/or various other materials configured to fill the fabric shell 102 and provide structure thereto. The support pillow 100 may comprise a first arm 104, a second arm 106, and a medial region 108 defined at least in part by the fabric shell 102 and the resilient fill material.

In some embodiments the support pillow 100 may further comprise a perimeter band 110 that extends around the perimeter of the support pillow (e.g., extending collectively and continuously around the first arm 104, the second arm 106, and the medial region 108). The perimeter band 110 may comprise fabric or any other material that may provide structure to the support pillow as discussed below. The perimeter band 110 may extend around the perimeter of the support pillow 100 between a first support surface 112 (see, e.g., FIG. 1) and an opposing second support surface 114 (see, e.g., FIG. 4) collectively defined by the first arm 104, the second arm 106, and the medial region 108. The perimeter band 110 may thus be affixed (e.g., directly affixed) to the first substantially laterally-extending panel 102A of the fabric material at the first support surface 112 and affixed (e.g., directly affixed) to the second laterally-extending panel 102B of the fabric material at the opposing second support surface 114.

The first support surface 112 and the opposing second support surface 114 of the support pillow 100 may be configured to support an infant. In one embodiment the support pillow 100 may be configured to be worn by a user when employed to support an infant. In particular, an opening 116 defined between the first arm 104 and the second arm 106 may be configured to provide a user with access to a well 118 at least partially surrounded by the first arm 104, the second arm 106, and the medial region 108. Accordingly, the user may spread the first arm 104 and the second arm 106 so as to allow his or her torso to enter through the opening 116. Normally, the first and second arms 104, 106 may be spaced apart though, in some instances, the first and second arms 104, 106 may be configured to contact each other. In some embodiments a seam 120 may extend around the perimeter band 110 between the first panel 102A and the second panel 102B of the fabric shell 102. The seam 120 may be configured to prevent tearing of the perimeter band 110 when the first arm 104 and the second arm 106 are pulled apart to increase a width of the opening 116 and/or provide additional functions as discussed below. Additional seams 122, 124 may be provided between the perimeter band 110 and the first panel 102A of the fabric shell 102 and between the perimeter band and the second panel 102B of the fabric shell. These seams 122, 124 couple the perimeter band 110 to the fabric shell 102 and further reduce the possibility of the perimeter band and fabric shell tearing when the first arm 104 and the second arm 106 are pulled away from each other. Other seams may be provided in the perimeter band 110, as necessary, to facilitate flexibility of the first and second arms, or to prevent tearing, wherein such seams, for instance, may extend transversely to the perimeter band 110.

The support pillow 100 may include an asymmetric configuration on opposing sides of a laterally-extending plane extending between the first and second support surfaces 112, 114. The asymmetric configuration may provide the support pillow with increased functionality. In particular, the first support surface 112 may define a lofted, arcuate, or otherwise rounded configuration, and the opposing second support surface 114 may define a substantially flat, planar configuration, as illustrated in FIG. 2. In this regard, in order to achieve the lofted configuration, the first panel 102A of the fabric shell 102 may define one or more larger dimensions relative to the second panel 102B of the fabric shell.

Further, in addition to the larger dimension first panel 102A, or in instances where the first and second panels 102A, 102B have the same or substantially similar dimensions, the resilient fill material may be sized and shaped to produce the lofted configuration at the side corresponding to the first support surface 112, and the resilient fill material may be sized and shaped to form a substantially planar configuration at the side corresponding to the opposing second support surface 114. That is, the surface of the resilient fill material disposed directly adjacent the first panel 102A of the fabric shell 102 may be configured to be lofted and generally rounded or arcuate. The surface of the resilient fill material disposed directly adjacent the second panel 102B of the fabric shell 102 may be configured such that it is generally flat. Thus, in one embodiment the resilient fill material may define a shape substantially similar to the ultimate shape of the support pillow 100 prior to being enclosed by the fabric shell 102.

However, in another embodiment the fabric shell 102 may be partially assembled with an aperture left open and configured to receive a loose fill material (e.g., feathers, cotton, etc. to form the lofted support surface) and/or a solid fill material (e.g., a solid foam material to form the substantially planar support surface). In instances where two or more different fill materials are implemented, such different fill materials may be separated, for example, by a fabric panel between each type of fill material, or separate compartments may be formed in the fabric shell 102 for receiving the different types of fill material. That is, in some aspects, the resilient fill material comprises a plurality of fill material components, with adjacent fill material components being separated by a fabric panel extending therebetween, and with the fabric panel being engaged with the fabric shell to prevent intermingling of the adjacent fill material components. For example, in one embodiment, two different fill material components may be implemented as the resilient fill material, and the fabric panel may be engaged with the inside surface of the fabric shell so as to extend in a lateral (i.e., substantially horizontal) plane to separate the two different fill material components from each other. In other aspects, particular types of fill material may be attached to the inside surface of the fabric shell 102 (i.e., a solid foam material may be glued to an appropriate inside surface of the fabric shell 102). Accordingly, such various types or forms of fill material may be used, either separately or in combination, to fill the fabric shell and cause the support pillow to expand to the dimensions allowed by the partially assembled fabric shell (i.e., the first panel 102A having a larger dimension than the second panel 102B). Accordingly, in some embodiments the shape of the support pillow 100 may be defined by one or both of the resilient fill material and the fabric shell 102.

Additionally, the shape of the support pillow 100 may be defined in part by the perimeter band 110. In this regard, the perimeter band 110 may provide structure to the support pillow and allow for a gradual transition between the perimeter band 110 and the first support surface 112 (having the lofted configuration) at the seam 122 and allow for a sharp transition between the perimeter band 110 and the opposing second support surface 114 at the seam 124. In this regard, the perimeter band 110 may be generally perpendicular to the opposing second support surface 114 and extend generally vertically when the opposing second support surface is configured in a horizontal orientation, for example, during use of the support pillow.

In some instances, the dissimilar dimensions of the first support surface 112 and the opposing support surface 114 result in an asymmetrical cross-section, which may allow for greater flexibility in how the pillow is used. In this regard, as noted above, the support pillow 100 may be configured to support an infant. The asymmetric configuration provides the opportunity to employ the first support surface 112 of the support pillow 100 with the lofted configuration to prop up an infant either on his or her back, side, or belly such that the infant may rest comfortably on the first support surface and, in some embodiments, partially within the well 118. Further, the opposing second support surface 114 with the flat, substantially planar configuration may be employed to support an infant during nursing, when the first and second arms are wrapped around a user's torso such that the user's torso is disposed in the well 118. Accordingly, the first support surface 112 and the opposing second support surface 114 may define differing configurations (e.g., lofted, and substantially planar, respectively) in order to provide the support pillow 100 with enhanced performance in the form of multiple modes of functionality depending on which support surface 112, 114 is employed to support the infant.

As illustrated in FIG. 3, in some embodiments the support pillow 100 may further comprise or define a pocket 126. The pocket 126 may be defined in the medial region 108 of the support pillow 100 in some embodiments. However, in other embodiments the pocket 126 may be defined in a different portion of the support pillow 100, such as the first arm 104 or the second arm 106. The pocket 126 may include a fabric liner 128 that defines the pocket and separates the pocket from the resilient fill material. The liner 128 may be sewn or otherwise attached directly to the outer periphery of the support pillow 100. In other aspects, the resilient fill material itself may define the pocket 126. The pocket 126 may extend into the support pillow 100 (e.g., into the medial region 108, the first arm 104, and/or the second arm 106) substantially parallel to the second support surface 114. In some instances, the opening into the pocket 126 may extend along a perimetric seam 120, 122, 124 associated with the perimeter band 110. In such instances, the pocket 126 formed in conjunction with the seam 120, 122, 124 may facilitate attachment of the fabric liner 128 of the pocket 126 and/or reduce the visibility of the opening into the pocket 126. Further, one or more transverse seams 129A, 129B may be provided proximate the pocket 126. The transverse seams 129A, 129B may be configured to prevent tearing (e.g., tearing of the perimeter band 110) proximate the pocket 126. In one embodiment the transverse seams 129A, 129B may align with the center of the pocket 126 across the width thereof, and a medial perimetric seam 120 may align with a center of the pocket across a height thereof.

The pocket 126 may be configured to receive an accessory device intended to enhance comfort of the infant and/or the user wearing the support pillow 100 about his or her torso and/or configured to perform other functions. For example, the pocket 126 may be used as a storage compartment for storing a pacifier, blanket, toy, etc. In this regard, the pocket 126 may be configured to receive, for example, a mechanized or other vibration unit configured to produce soothing vibrations, a sound device configured to produce music and/or peaceful or familiar sounds configured to soothe and induce sleep in infants, a combination device including a mechanized or other (i.e., electrically-driven) vibration unit and a sound device, a heating or cooling device and/or other accessory device. The vibration unit may comprise a battery-operated motor housed within a protective shell, wherein the shell may include a manually depressible activator or actuator or any other suitable switch or actuator, such as a lever switch or a motion switch/actuator. When the pocket 126 is open, the user may activate the accessory device while it is disposed within the pocket by reaching his or her hand inside the pocket and manually depressing the actuator or actuating the switch. In an alternate embodiment, the user may activate the accessory device by applying pressure to the support pillow 100 about the location of the pocket 126 to depress the actuator or actuate the switch, without reaching inside the pocket. In some embodiments a closure may be included at the opening of the pocket 126, such as a zipper, hook and loop fastener, or other device configured to releasably hold the pocket shut.

As noted above, in some embodiments the support pillow 100 may be configured to receive the torso of a user in the well 118. In this regard, as further noted above, the user may spread the first arm 104 and the second arm 106 apart to form or increase the width of the opening 116 between the first arm and the second arm so that the user's torso may be received therein. In order to facilitate bending of the first arm 104 and the second arm 106, the first arm may include a first laterally-extending indentation 130A, and the second arm may include a second laterally-extending indentation 130B, wherein each indentation 130A, 130B may be defined through interaction between appropriately-configured first and second panels 102A, 102B and the perimeter band 110, as illustrated in FIG. 4. The indentations 130A, 130B may locally reduce cross-sectional areas of the first arm 104 and the second arm 106, along a plane extending perpendicularly to the second panel 102B, such that the first arm and the second arm are easier to bend or deform at the indentations (i.e., form "living hinges") and use of the support pillow 100 may be facilitated by allowing the space between the first and second arms 104, 106 to be more readily increased to facilitate entry into/exit from the well 118 through the opening 116.

FIGS. 5-7 illustrate alternate embodiments of the support pillow. The embodiments of the support pillows illustrated in FIGS. 5-7 may be substantially similar to the embodiment of the support pillow 100 illustrated in FIGS. 1-4, with the exception of the differences described below. In this regard, elements in FIGS. 5-7 corresponding to those included in the first embodiment of the support pillow 100 are shown with a reference numeral that is the same as those appearing in FIGS. 1-4 with the exception of the first digit, which is incremented based on the embodiment.

FIGS. 5 and 6 illustrate a support pillow 200 according to a second embodiment. The support pillow 200 may include a cover 232 that substantially entirely surrounds, collectively, the first arm 204, the second arm 206, and the medial region 208 of the support pillow defined by the fabric shell and resilient fill material, as discussed above. As illustrated, in some embodiments the cover 232 may include a first panel 234 at the first support surface 212, a second panel 236 at the opposing second support surface 214, and a perimeter band 238 that respectively and substantially correspond in size and shape to the first and second panels of the fabric shell and the perimeter band of the support pillow 200. The cover 232 (and/or the fabric shell) may be produced from materials that are water resistant, stain resistant, machine washable, and/or waterproof in some embodiments, although various other materials and fabrics (i.e., textured materials, fireproof materials, or the like) may be employed in other embodiments.

In some embodiments the cover 232 may be permanently affixed to the fabric shell of the support pillow 200. However, in other embodiments the cover may be selectively removable and/or machine washable. In this regard, FIG. 6 illustrates a closure 240 in the form of a zipper that is configured to open and close to allow the cover 232 to releasably secure the filled fabric shell therein. Various other embodiments of closures may be employed to releasably secure the cover 232 in a closed configuration, such as hook and look fasteners, snap fasteners, buttons, etc. The closure 240 may extend around all or a portion of the perimeter of the support pillow 200 in some embodiments. The closure 240 may be configured to provide access to the pocket 226 defined in the support pillow 200, or a separate closure and/or opening may be provided to enable access to the pocket. In this regard, the support pillow 200 may define a resealable opening (at the closure 240, or a separate closure) that is configured to align with the pocket 226 defined in the medial region 208.

The cover 232 may include a handle 242, though such a handle may be included in addition to or instead of a similar handle on the fabric shell of the support pillow (i.e., in some embodiments, not including a cover 232, the fabric shell of the support pillow itself may include such a handle). As such, aspects herein involving a handle 232 may also be applicable to the fabric shell of the support pillow in instances where a cover 232 is not provided. The handle 242 may be useable to carry the support pillow 200. As illustrated in FIG. 6, in some embodiments the handle 242 may extend along and/or across the pocket 226 at the perimeter of the support pillow 200. Further, in some embodiments the handle 242 may define one or more loops 244A-D, in cooperation with the cover 232 (i.e., through spaced-apart seams securing the handle member to the cover 232). The loops 244A-D, which may be positioned at opposing ends of the handle 242, may be configured to attach one or more components or peripheral accessories to the cover 232 of the support pillow 200, such as, for example, child's toys.

FIG. 7 illustrates an additional embodiment of the support pillow 300. The support pillow 300 may comprise an adjustment mechanism 346 configured to adjust at least one of a width of the opening 316 defined between the first arm 304 and the second arm 306 and an area of the open well 318. The adjustment mechanism 346 may comprise an elongated flexible member 348 extending from the first arm 304 around the well 318 to the second arm 306 and a fixation member 350 coupled to one or both of the first arm and the second arm and configured to releasably engage the elongated flexible member at a user-selectable position. In one embodiment one of the elongated flexible member 348 and the fixation member 350 comprises a hook material, and the other of the adjustable elongated member and the fixation member comprises a loop material. However, in other embodiments, buttons, clips, snap fasteners, cords and clasps and/or other mechanisms may be employed to define the adjustment mechanism 346.

Further, the elongated flexible member 348 may define an exposed section disposed at one or both of the first arm 304 and the second arm 306 and an internal section disposed inside the fabric shell 302 and partially surrounding the well 318. In this regard, the elongated flexible member 348 may extend substantially parallel and adjacent to the perimeter band 310 on inside surfaces (at the internal section of the elongated flexible member) and outside surfaces (at the exposed section(s) of the elongated flexible member) thereof. The adjustment mechanism 346 may be configured to decrease the area of the well 318 and the width of the opening 316 between the first arm 304 and the second arm 306 when a length of the exposed section of the elongated flexible member 348 is increased relative to a length of the internal section of the elongated flexible member. In this regard, a user may detach the elongated flexible member 348 from the fixation member 350 at one of the arms 304, 306, pull on the elongated flexible member so as to increase the length of the exposed portion of the elongated flexible member, and reattach the elongated flexible member to the fixation member. This process may be repeated for the other of the arms 304, 306 in embodiments of the support pillow 300 employing elongated flexible members 348 that are detachable at both of the ends thereof. When an end of the elongated flexible member 348 is pulled, a compressive force applied by the elongated flexible member to the resilient fill material causes a reduction in the width of the opening 316 between the first arm 304 and the second arm 306 as well as the area of the well 318. When one or more ends of the elongated flexible member 348 are released from the fixation member 350 after the elongated flexible material has been placed in tension, the resilient fill material expands from the compressive state allowing the support pillow 300 to return to its original shape.

As further illustrated in FIG. 7, in some embodiments the support pillow may further comprise one or more additional transverse seams 352A, 352B. These transverse seams 352A, 352B may be positioned on the perimeter band 310 across from, and centered with, the opening 316 between the first arm 304 and the second arm 306 in some embodiments. In this regard, the transverse seams 352A, 352B may be oriented perpendicularly to the perimeter band 310 at one or more locations around the well 318 where stress may concentrate when the first arm 304 and the second arm 306 are pulled apart. Accordingly, the transverse seams 352A, 352B may be configured to withstand the forces (e.g., tensile forces) applied thereto during movement of the first arm 304 and the second arm 306 apart from one another.

In an additional embodiment a method for forming a support pillow, such as the support pillows 100, 200, 300 described above, is provided. The method may include providing a resilient fill material and a fabric shell comprising a first panel and a second panel, and coupling the first panel of the fabric shell to the second panel of the fabric shell with the fill material therebetween so as to at least partially enclose the fill material with the fabric shell and define a support pillow comprising a first arm, a second arm, and a medial region that connects the first arm to the second arm. The first arm, the second arm, and the medial region may partially or substantially surround and define a well, wherein the first arm and the second arm may be configured to be separable to provide a user with access to the well therebetween, or wherein the first arm and second arm may define an opening therebetween to provide access to the well. Further, the first arm, the second arm, and the medial region may define a first support surface with a lofted configuration and an opposing second support surface with a substantially planar configuration.

In some embodiments the method may further comprise coupling a perimeter band to the first panel of the fabric shell and to the second panel of the fabric shell such that the perimeter band extends around the perimeter of the support pillow between the first support surface and the opposing second support surface. Also, the method may include coupling an adjustment mechanism to the support pillow, wherein the adjustment mechanism is configured to adjust at least one of a width of the opening between the first arm and the second arm and an area of the well. Coupling the adjustment mechanism to the support pillow may comprise enclosing an internal section of an elongated flexible member between the first panel and the second panel of the fabric shell so as to partially surround the well, and releasably coupling an exposed section of the elongated flexible member to one of the first arm and the second arm.

As noted above, in some embodiments the support pillows disclosed herein are configured for use in conjunction with one or more accessory devices, such as a vibration unit. In this regard, the support pillows disclosed herein may include features configured to attach the accessory devices to the support pillows, which are hereinafter referred to as attachment mechanisms. The attachment mechanism may be configured to attach the accessory device to at least one of the first arm, the second arm, and the medial region of the support pillow in some embodiments. In other embodiments, the accessory device attached to the support pillow may be arranged to direct a perceptible effect (i.e. a sensory effect) to at least one of the first arm, the second arm, and the medial region, including, for example, the first substantially laterally-extending support surface, the second laterally-extending support surface, and the perimeter band. Further, in some embodiments the attachment mechanism may be configured to attach the accessory device to the support pillow such that the accessory device avoids direct contact with the first substantially laterally-extending support surface and/or the second laterally-extending support surface. In this regard, as noted above, the support surfaces may be employed to support a child. Accordingly, it may be desirable to avoid direct contact between accessory device and one or both of the support surfaces such that the child and the accessory device are not brought into contact. For example, direct contact between a child and a vibration unit may be uncomfortable for a child. Example embodiments of attachment mechanisms and accessory devices that may be employed in conjunction with the above-described support pillows and various other embodiments of support pillows are illustrated in FIGS. 8-34.

FIG. 8 illustrates an embodiment of a support pillow 400 in which the attachment mechanism comprises a plurality of pockets 426 positioned in conjunction with the perimeter band 410 around the arms 404, 406, the medial region 408, and the well 418. In particular, the pockets 426 are positioned externally to the fabric shell 402 in the embodiment illustrated in FIG. 8. For example, the pockets 426 may be sewn or otherwise attached to the exterior of the perimeter band 410.

As illustrated in FIG. 9, the support pillow 400 may be combined with an accessory device 454 to define a support pillow assembly 400'. In this regard, the accessory device 454 may be received in the pocket 426. In particular, each of the pockets 426 may extend substantially perpendicularly to the support surfaces 412, 414. Further, each pocket 426 may define an opening 456 that may be opened and closed with a zipper 458. However, various other closure mechanisms may be employed in other embodiments, such as magnets, snap fasteners, elastic bands sewn into the openings, and hook and loop fasteners. Alternatively, the opening may not include a closure member in other embodiments (i.e., may be configured to implement overlapping fabric layers).

As described above, in some embodiments the pockets may be coupled to the exterior of the fabric shell. Conversely, FIG. 10 illustrates an embodiment of a support pillow 500 wherein the pockets 526 extend inside of the fabric shell 502. In this regard, as illustrated in FIG. 11, when the accessory device 554 is combined with the support pillow 500 to define a support pillow assembly 500', the accessory device may be positioned inside of the perimeter band 510. In some embodiments the pocket may comprise a liner that retains the accessory device proximate the perimeter band. In another embodiment the resilient fill material may function to retain the accessory device 554 in a position proximate the perimeter band without use of a liner.

FIG. 12 illustrates an alternate embodiment of a support pillow 600 in which the pockets 626 extend inside the fabric shell 602. However, in this embodiment the pockets 626 extend substantially parallel to the first substantially laterally-extending support surface 612 and the second laterally-extending support surface 614. The pockets 626 may extend through the peripheral band 610 at one or more locations around the perimeter of the support pillow 600. In other instances, the pockets 626 may extend substantially perpendicularly to the first substantially laterally-extending support surface 612 and/or the second laterally-extending support surface 614, such that the pocket extends medially into the fill material (i.e., medially with respect to the perimeter band).

FIG. 13 illustrates a support pillow assembly 600' that includes the support pillow 600 of FIG. 12 and an accessory device 654. As illustrated, the accessory device 654 may be received in one of the pockets 626 of the support pillow 600 in a substantially horizontal configuration. However, the pockets 626 may extend into the support pillow 600 at various angles relative to the first 612 and second 614 laterally extending support surfaces depending on a desired configuration thereof.

FIG. 14 illustrates an embodiment of a support pillow 700 that is substantially similar to the embodiment of the support pillow 600 illustrated in FIG. 12. However, in additional to providing pockets 726 at multiple locations about the perimeter of the peripheral band 710, the support pillow 700 also includes pockets at multiple heights thereon. In this regard, the illustrated embodiment of the support pillow 700 includes pockets 726A at a first height and pockets 726B at a second height. By configuring the pockets 726 in this manner, a distance between the pockets 726A at the first height and the first substantially laterally-extending support surface 712 (and the second laterally-extending support surface 714) differs from a distance between the pockets 726B at the second height and the first substantially laterally-extending support surface (and the second laterally-extending support surface). Accordingly, while the embodiments of support pillows illustrated in FIGS. 8-13 provide for placement of an accessory device at multiple positions about the periphery of the support pillows, the embodiment of the support pillow 700 illustrated in FIG. 14 additionally provides for the placement of accessory devices at multiple heights.

In the embodiments of support pillow assemblies described above, the attachment mechanism has generally been described as being a pocket. However, in other embodiments various other attachment mechanisms may be additionally or alternatively employed to attach the accessory device to the support pillow. For example, FIG. 15 illustrates an embodiment of the support pillow assembly 800' in which a strap 860 is employed to attach the accessory device 854 to the support pillow 800. In the illustrated embodiment the strap 860 is configured to removably hold the accessory device 854 to the peripheral band 810.

As illustrated, the strap 860 may be fixed to the support pillow 800 such that the accessory device is removable therefrom in some embodiments. For example, in one embodiment the strap 860 may be elastic and secured to the support pillow 800 at both ends 860A, 860B of the strap. In another embodiment the strap 860 may be secured to the support pillow 800 at a first end 860A and removably attached to the support pillow at a second end 860B. For example, the second end 860B of the strap 860 and a corresponding portion of the support pillow 800 may comprise cooperating portions of a snap fastener or a hook and loop fastener. In embodiments in which the strap 860 is fixed to the support pillow 800 (at one or both ends 860A, 860B), the accessory device 854 may be removable from the strap. Accordingly, when the accessory device 854 is removed, the strap 860 may be employed to retain other items such as a baby bottle. Further, the length of the strap 860 may be adjustable such that the strap may securely engage the accessory device 854 and/or other items at different distances.

As illustrated in FIG. 16, in another embodiment of the support pillow assembly 900' the strap 960 may be fixed to the accessory device 954 and removable from attachment with the support pillow 900. In this regard, the strap 960 may be secured to the accessory device 954 at both ends 960A, 960B, and the strap may be elastic. Therefore, by way of example, the strap 960 may wrap around an arm 904, 906 of the support pillow 900 to secure the accessory device 954 thereto. Alternatively, the strap 960 may be fixed to the accessory device 954 at a first end 960A, and removably secured to the accessory device at a second end 960B. For example, the second end 960B of the strap 960 and a corresponding portion of the accessory device 960 may comprise cooperating portions of a snap fastener or a hook and loop fastener. Further, the length of the strap 960 may be adjustable to allow for use of the accessory device 954 at various placements on and/or at different distances from the support pillow 900.

In another embodiment of the support pillow assembly 1000' illustrated in FIG. 17, the attachment mechanism comprises a clip 1062 coupled to the accessory device 1054 and configured to compressively or otherwise removably engage the support pillow 1000. For example, the clip 1062 may be configured to pinch the exterior of the support pillow 1000 such as one of the arms 1004, 1006 or the medial region 1008. Alternatively, the clip 1062 may pinch an internal portion of the support pillow 1000 such as the resilient fill material, or engage a fabric tab extending from a surface of the support pillow 1000.

In another embodiment cooperating portions of hook and loop fasteners, snap fasteners, magnets, etc. may be employed to directly or indirectly attach the accessory device to the support pillow. For example, FIG. 18 illustrates an embodiment of the support pillow assembly 1100' in which a portion 1164A of a hook and loop fastener is attached to the support pillow 1100 and a portion 1164B of the hook and loop fastener is attached to the accessory device 1154. Accordingly, as illustrated in FIG. 19, the portions 1164A, 1164B of the hook and loop fastener may cooperate to attach the accessory device 1154 to the support pillow 1100. Further, although the portion 1164A of the hook and loop fastener is illustrated as being positioned on the exterior of the support pillow 1100, in other embodiments the portion of the fastener attached to the support pillow may be attached to an interior portion thereof. For example, a hook and loop fastener may be included in a pocket that extends into the support pillow such that the accessory device may be attached therein.

The above-described embodiments of attachment mechanisms have generally been described and shown in terms of embodiments in which the accessory device is coupled to, or received through, the perimeter band. However, this need not be the case in all embodiments. For example, FIG. 20 illustrates an embodiment of the support pillow assembly 1200' in which the accessory device 1254 is received through the first substantially laterally-extending support surface 1212, and in other embodiments the accessory device may be received through the second laterally-extending support surface.

For example, FIG. 20 illustrates an embodiment of the support pillow assembly 1200' in which the attachment mechanism comprises a cavity 1266 defining an opening 1268 at the first substantially laterally-extending support surface 1212. As illustrated in FIG. 21, the cavity 1266 and the accessory device 1254 may be configured such that when the accessory device is received in the cavity, the accessory device is recessed relative to the first substantially laterally-extending support surface. In this regard, by avoiding protrusion from, or extension to, the first substantially laterally-extending support surface, direct contact between the accessory device and a child or caregiver may be avoided, while the accessory device 1254 may still be arranged to direct the perceptible effect to at least one of the first arm 1204, the second arm 1206, and the medial region 1208. In other embodiments the cavity may be positioned at another location on the support pillow (e.g., on the bottom or side). The accessory device may define a dimension that is slightly larger than a dimension of the cavity, such that the accessory device is held therein by interference fit. Alternatively or additionally, the opening of the cavity may include an elastic band or other mechanism configured to stretch and allow for insertion and removal of the accessory device. Further, in other embodiments the cavity may be recessed relative to another portion of the support pillow including, for example, the second laterally extending support surface, or the perimeter band.

In some embodiments the attachment mechanism may additionally or alternatively comprise a tether. In this regard, FIG. 22 illustrates an embodiment of the support pillow assembly 1300' in which a tether 1370 is configured to couple the accessory device 1354 to the support pillow 1300. Further, the attachment mechanism may comprise a pocket 1326. In this regard, the tether 1370 may be employed with various other attachment mechanisms disclosed herein. Thus, for example, the accessory device 1354 may be removable from the pocket 1326 to allow for changing of batteries, etc., and the tether 1370 may help prevent loss of the accessory device.

Further, the tether may be configured to allow for attachment of the accessory device to the support pillow at a variety of different positions. For example, in embodiments in which the support pillow comprises multiple pockets, the tether may be configured to have sufficient length to allow for insertion of the accessory device into any of the pockets. Further, the tether may be permanently or removably coupled to each of the accessory device and the support pillow. For example, when the tether is removable from the accessory device, the tether may be used to couple other objects to the pillow such as, for example, a pacifier or a toy, when the accessory device is removed from the tether.

Accordingly, the various attachment mechanisms disclosed herein provide for a variety of manners and methods for attachment of an accessory device to the support pillow. In this regard, it should be understood that the illustrated embodiments are provided for example purposes only. Various other configurations of the attachment mechanisms may be employed in other devices. For example, the pockets may extend into the support pillow at other locations, extend to other depths within the pillow, extend at different angles (e.g., perpendicular to the support surface), etc.

As noted above, various embodiments of accessory devices may be employed in accordance with the support pillow assemblies disclosed herein. As further noted above, in one embodiment the accessory device may comprise a vibration unit. In this regard, FIG. 23 illustrates an exploded view of an example embodiment of a vibration unit 1454. The vibration unit 1454 may comprise a housing 1472 including a first portion 1472A and a second portion 1472B, which may be configured to substantially enclose the remainder of the vibration unit. The vibration unit 1454 may further comprise a motor 1474 coupled to an eccentric mass 1476. The motor 1474 may also be electrically connected to a battery 1478 (or other suitable power source) and a switch 1480. Thus, when the switch 1480 is actuated by depressing a switch cover 1482, electricity may be supplied by the battery 1478 to actuate the motor 1474 and thereby rotate the eccentric mass 1476 to produce vibrations. Vibrations produced by the vibration unit 1454 may be employed to sooth an infant, for example, by attachment to a support pillow as described above such that the vibrations are directed to one of the first arm, the second arm, and the medial region. For example, the vibrations may be directed to the first substantially laterally-extending surface of the support pillow so as to provide a desired perceptible effect. The switch may be actuatable through compression of a support pillow in which the vibration unit is positioned, through manual depression of the switch cover 1482, and/or via actuation of a wired or wireless remote controller in some embodiments.

As illustrated in FIG. 23, the housing 1472 may be substantially devoid of corners and sharp edges when the housing is in an assembled configuration. In this regard, as noted above, in some embodiments the vibration unit 1454 may be attached to a support pillow at an interior or exterior portion thereof. Accordingly, by avoiding use of corners and edges, uncomfortable contact therewith may be avoided. However, in other embodiments, such as the embodiment of the support pillow assembly 1500' illustrated in FIG. 24, the vibration unit 1554 may define other configurations such as a rectangular configuration.

FIG. 25 illustrates an embodiment of a support pillow assembly 1600' comprising a vibration unit 1654 that includes a vibration transmitter, configured to transmit vibrations produced by the vibration unit through the support pillow 1600, at least to the first substantially laterally-extending surface. In particular, in the illustrated embodiment the vibration transmitter comprises a first extension 1684 configured to transmit vibrations to the first arm 1604 of the support pillow 1600 and a second extension 1686 configured to transmit vibrations to the second arm 1606 of the support pillow. Further, the vibration unit 1654 may be positioned in the medial region 1608 of the support pillow. Accordingly, vibrations may be transmitted substantially throughout the support pillow 1600 by the extensions 1684, 1686, rather than only proximate to the vibration unit 1654.

In some embodiments the vibration transmitter may be detachable from the vibration unit. Accordingly, if a user desires a more concentrated vibration proximate to the vibration unit, the vibration transmitter may be removed. Further, in some embodiments the configuration of the vibration transmitter may be adjustable. For example, a distance between the first extension 1684 and the second extension 1686 (e.g., a distance between the distal ends of the extensions 1688 may be adjustable). Accordingly, the vibration transmitter may allow for movement of the two extensions 1684, 1686 such that the arms 1604, 1606 may remain flexible as discussed above. In this regard, the extensions 1684, 1686 may be formed from a flexible material such as plastic. Further, in some embodiments the extensions 1684, 1686 may include a ratcheting mechanism or other mechanism configured to retain the extensions in user-selectable positions. Thus, for example, a user may employ the extensions 1684, 1686 to retain the arms 1604, 1606 in a desired position (e.g., wherein the arms are relatively close to one another, or spread out from one another).

FIG. 26 illustrates an embodiment of the support pillow assembly 1700' in which the accessory device comprises a plurality of vibration units 1754A-E which may or may not be interconnected. In one embodiment the vibration units 1754A-E may be selectively positioned by a user. Thus, as illustrated, the vibration units 1754A-E may be spread out through the support pillow 1700. Alternatively, a user may position the vibration units 1754A-E relatively close to one another such that an intense vibration is provided at one or more selected positions.

The vibration units 1754A-E may each include a respective switch or controller in some embodiments, or a single controller 1790 may be employed to operate any or all of the vibration units. In one embodiment the controller may be positioned at one of the vibration units 1754A-E, whereby the controller is configured to control one or more of the vibration units controls either separately or as part of a group of one or more of the vibration units. In another embodiment, as illustrated, the controller 1790 may be configured to operate the vibration device remotely, through either a wired or wireless connection. In this regard, each of the accessory devices disclosed herein may include a remote controller in some embodiments. The remote controller may be located inside or outside of the support pillow, may be fixed or detachable from the accessory unit, and/or the entire accessory device and remote controller may be fixed to or removable from the support pillow.

The controller 1790 may be configured to turn all of the vibration units 1754A-E on and off at the same time, and/or the controller may be configured to at least partially independently control the vibration units. For example, a single actuation of the controller 1790 may be configured to turn on one of the vibration units 1754A-E, while a second actuation of the controller may be configured to turn on two of the vibration units or a second one of the vibration units individually, etc.

The vibration units may not be physically connected or interconnected in some embodiment, but may still be controlled by the same controller. Multiple vibration units may also each be independently controlled (e.g., via a power button or controller for each vibe). This may be in addition to, or as an alternate of a remote controller which controls any or all of the vibration units.

FIG. 27 illustrates an alternate embodiment in which the accessory device comprises both a vibration unit 1854 and a speaker 1892 (though such an embodiment can also include only the speaker 1892 without the vibration unit 1854). Accordingly, the accessory unit may provide for output of vibrations and/or audio output (e.g., music, soothing nature sounds, an alarm, etc.) as the perceptible effect(s) directed to at least one of the first arm, the second arm, and the medial region of the support pillow. The accessory device may also include components configured to record or capture audio. Thus, in one embodiment the speaker 1892 may be employed to output a caregiver's voice (perceptible effect) in order to sooth a child. Further, the accessory device may include a timer in some embodiments that allows a caregiver to preset a length of time for the speaker 1892 to output audio and/or for the vibration unit 1890 to vibrate. Additionally, the volume of the audio output from the speaker 1892 may be adjustable. Also, the vibration unit 1854 may be configured to vibrate in synchronization with the audio output from the speaker 1892. For example, the vibration unit 1854 may vibrate faster when the beat of music output by the speaker 1892 gets faster or the volume increases, and/or the vibration unit may vibrate with each beat of the music. Although the vibration unit 1854 and the speaker 1892 are illustrated as being separate components in FIG. 27, in another embodiment (as illustrated in FIG. 28), the speaker 1992 may be integrated into the vibration unit 1954.

In another embodiment the speaker 1892 may be configured to output heartbeat sounds. Further, the vibration unit 1890 may be configured to pulse in synchronization with the heartbeat sounds. Accordingly, the support pillow assembly 1800' may mimic a womb environment so as to sooth a child.

FIG. 29 illustrates an embodiment of the support pillow assembly 2000' in which the accessory unit comprises a plurality of lighting elements 2094A-G (e.g., light emitting diodes or bulbs). As illustrated, the lighting elements may be configured to extend proximate the first substantially laterally-extending support surface 2012 (and/or the second laterally-extending support surface). Accordingly, the lighting elements may be configured to emit light from the support pillow 2000 to provide a perceptible effect. For example, the lighting elements 2094A-G may emit light that shines through the fabric shell, which may provide a pleasing ornamental appearance and/or facilitate use of the support pillow 2000 in low light conditions. The light may be emitted through various portions of the support pillow 2000, such as the first arm 2004, the second arm 2006, the medial region 2008, including, for example, through the perimeter band 2010, the first substantially laterally-extending support surface 2012, and/or the second laterally-extending support surface. In some embodiments the lights may be configured to shine outward onto the walls or floor or other portions of a surrounding environment.

In some embodiments the lighting elements 2094A-G may be adjustable automatically or manually in terms of brightness, color, blinking versus steady, and/or other factors. Further, in some embodiments the lighting elements 2094A-G may be configured to blink to provide a pleasing appearance which may capture the interest of a child (e.g., in synchronization with the beats of music output from the accessory device or an external music source). Although the lighting elements are illustrated as being positioned inside the fabric shell and thereby shining therethrough, in another embodiment the lighting elements may extend outside the fabric shell, since the lighting elements may not emit vibrations that may be unpleasant when applied directly to the body of a child.

FIG. 30 illustrates an embodiment of the support pillow assembly 2100' in which the accessory device comprises a thermal element 2196 configured to affect a temperature of the support pillow 2100 as a perceptible effect provided by the accessory device. In the illustrated embodiment, the thermal element is positioned proximate the first substantially laterally-extending surface 2112 (e.g., underneath the fabric shell), such that the thermal element may affect a temperature of the first substantially laterally extending support surface. For example, the thermal element 2196 may comprise a heating element configured to heat the first substantially laterally-extending support surface 2112 and/or a cooling element configured to cool the first substantially laterally-extending support surface. The thermal element 2196 may be battery powered or powered by household alternating current. The thermal element 2196 may include a controller that allows for adjustment of the temperature provided thereby.

Accordingly, a user may employ the thermal element 2196 to control a temperature at the first substantially laterally-extending support surface 2112 to warm or cool a child as desired. In another embodiment, a first thermal element may be provided at the first substantially laterally-extending support surface, and a second thermal element may be provided at the second laterally extending support surface. The first and second thermal elements may be independently controllable to provide, for example, a pleasing temperature for a child at the first substantially laterally extending support surface, and a pleasing temperature for a caregiver at the second laterally-extending support surface. In this regard, for example, a warming sensation may be desirable for the child, whereas the caregiver may prefer a cooling sensation.

As illustrated in FIG. 31, in some embodiments the accessory device may comprise a fixed portion 2298A that is fixed to the support pillow 2200 and a removable portion 2298B that may be removed from (see, e.g., FIG. 31), or attached to (see, e.g., FIG. 32) the support pillow. In some embodiments the removable portion comprises a vibration mechanism (such as the above-described motor and eccentric mass). Further, as illustrated in FIGS. 33 and 34, in some embodiments the removable portion 2398B is configured to hold a battery. In this regard, in some embodiments the accessory device may be configured to operate upon attachment of the removable portion 2398B to the fixed portion 2398A.

Various other embodiments of accessory devices and corresponding attachment mechanisms are also provided. For example, the accessory device may comprise a free-floating or otherwise unsecured vibration unit removably or permanently disposed in the fill material of the support pillow. In another embodiment a cavity or slot formed in the fill material may be configured to receive a vibration unit. For example, the fill material may comprise a solid piece of foam with a cavity or slot formed therein, and configured to receive one or more accessory devices such as a vibration unit.

In another embodiment the accessory device may comprise an aromatic element configured to release a scent (e.g., calming smell) to the support pillow as the perceptible effect. The aromatic element may be linked to another accessory device in one embodiment. For example, when the above-described thermal element 2196 heats the support pillow, the thermal element may heat a scented oil associated with the aromatic element to release a scent. In another embodiment the aromatic element may be independently operated. For example, the aromatic element may comprise a fan that draws air past a scented oil or scented material. The aromatic element (in addition to the various other accessory devices disclosed herein) may be configured to release the scent (or the accessory device may be configured to provide the perceptible effect) in response to movement of the support pillow or pressure on the support pillow (e.g. a baby lying on the pillow). In one embodiment the aromatic element may comprise a bag (or other container) of potpourri which is configured to release a scent therefrom according to the general nature thereof. In such instances, for example, compression of the support pillow during use may draw air through the support pillow and the potpourri so as to distribute the scent thereof In another embodiment a method for forming a support pillow assembly is provided. The method may comprise providing a support pillow comprising a resilient fill material and a fabric shell at least partially enclosing the fill material. The resilient fill material and the fabric shell may define a first arm, a second arm, and a medial region that connects the first arm to the second arm. Further, the first arm, the second arm, and the medial region may at least partially surround and collectively define a well. Also, the first arm, the second arm, and the medial region may define a first substantially laterally-extending support surface and an opposing second laterally-extending support surface in some embodiments.

The method may also include providing an accessory device, providing an attachment mechanism, and attaching the accessory device to at least one of the first arm, the second arm, and the medial region of the support pillow with the attachment mechanism such that the accessory device is arranged to direct a perceptible effect to at least one of the first arm, the second arm, and the medial region and/or avoids direct contact with the first substantially laterally-extending support surface. Accordingly, as noted above, direct contact between a child and/or caregiver and the accessory device may be avoided. This may be preferable in some embodiments to avoid, for example, directly applying heat or vibrations to the caregiver or child.

In some embodiments of the method, the accessory device may comprise a vibration unit, and a vibration transmitter comprising a first extension and a second extension. In this embodiment the method may further comprise inserting the first extension into the first arm and inserting the second extension into the second arm. In another embodiment the attachment mechanism may comprise a pocket, and attaching the accessory device may comprise inserting the accessory device into the pocket.

Many modifications and other embodiments of the disclosure set forth herein will come to mind to one skilled in the art to which the disclosure pertains having the benefit of the teachings presented in the foregoing descriptions. Therefore, it is to be understood that the disclosure is not to be limited to the specific embodiments described herein and that modifications and other embodiments are intended to be included within the scope of the appended claims. Although specific terms are employed herein, they are used in a generic and descriptive sense only and not for purposes of limitation.

The invention claimed is:

1. A nursing and infant support pillow assembly, comprising:
   a resilient fill material;
   a fabric shell enclosing the resilient fill material,
   the resilient fill material and the fabric shell defining a first arm, a second arm, and a medial region connecting the first arm to the second arm,
   the first arm, the second arm, and the medial region defining a first laterally-extending support surface and an opposing second laterally-extending support surface;
   wherein the fabric shell comprises a perimeter band extending between the first laterally-extending support surface and the opposing second laterally-extending support surface and about a perimeter defined by the first arm, the second arm, and the medial region, and wherein a pocket is defined in the fabric shell and accessible through an opening along the perimeter band; and
   a thermal element configured to be positioned within the pocket defined within the fabric shell and between the first laterally-extending support surface and the opposing second laterally-extending support surface such that the thermal element is arranged to affect a temperature of at least one of the fabric shell and the fill material.

2. The pillow assembly of claim 1, further comprising a cover configured to surround the fabric shell.

3. The pillow assembly of claim 2,
   wherein the cover defines a reclosable opening configured to provide access to the pocket.

4. The pillow assembly of claim 2, wherein cover is configured to conform to the first arm, the second arm, and the medial region of the pillow.

5. The pillow assembly of claim 1, wherein the pocket extends into the resilient fill material such that the resilient fill material surrounds the pocket except at an opening thereto.

6. The pillow assembly of claim 1, wherein the pocket extends inside the fabric shell.

7. The pillow assembly of claim 1, wherein the pocket extends along the fabric shell, between the resilient fill material and the fabric shell.

8. The pillow assembly of claim 1, further comprising a closure arranged about the opening to removably secure the thermal element within the pocket.

9. The pillow assembly of claim 8, wherein the closure comprises at least one of:
   a magnet;
   a snap fastener;
   a zipper; and
   a hook and loop fastener.

10. The pillow assembly of claim 1, wherein the thermal element is configured to direct a perceptible thermal effect outwardly of the pocket.

11. The pillow assembly of claim 1, wherein the thermal element comprises a controller configured to adjust the temperature provided by the thermal element.

12. The pillow assembly of claim 1, wherein the pocket is arranged to extend substantially perpendicularly to at least one of the first laterally-extending support surface and the opposing second laterally-extending support surface.

13. The pillow assembly of claim 1, wherein the thermal element is arranged to direct a perceptible thermal effect externally to the fabric shell.

14. The pillow assembly of claim 1, wherein the thermal element is configured as one of a heating element configured to emit heat as a perceptible thermal effect and a cooling element configured to dissipate heat as a perceptible thermal effect.

15. The pillow assembly of claim 1, wherein the pocket is positioned closer to a first one of the support surfaces than a second one of the support surfaces, the thermal element thereby being configured to affect the temperature of the first one of the support surfaces to a greater extent than the second one of the support surfaces.

16. A method for forming a nursing and infant support pillow assembly, the pillow assembly comprising a resilient fill material and a fabric shell enclosing the resilient fill material,
the resilient fill material and the fabric shell defining a first arm, a second arm, and a medial region connecting the first arm to the second arm,
the first arm, the second arm, and the medial region defining a first laterally-extending support surface and an opposing second laterally-extending support surface, the method comprising:
positioning a thermal element inside of the fabric shell between the first laterally-extending support surface and the opposing second laterally-extending support surface of the pillow assembly such that the thermal element is arranged to affect a temperature of the first arm, the second arm, and the medial region of the pillow; and
inserting the fabric shell into a cover such that the cover surrounds the resilient fill material, the fabric shell, and the thermal element.

17. The method of claim 16, comprising forming a pocket at least partially defined by the fabric shell, the pocket being configured to receive the thermal element therein.

18. The method of clam 17, comprising inserting the thermal element, comprising one of a heating element configured to emit heat as a perceptible thermal effect and a cooling element configured to dissipate heat as a perceptible thermal effect, into the pocket.

19. The method of claim 17, comprising arranging the thermal element within the pocket in order for the thermal element to direct a perceptible thermal effect externally to the fabric shell.

20. The method of claim 17, comprising arranging the thermal element within the pocket in order for the thermal element to direct a perceptible thermal effect outwardly of the pocket.

21. The method of claim 17, wherein the fabric shell comprises a perimeter band extending between the first laterally-extending support surface and the opposing second laterally-extending support surface, and about a perimeter defined by the first arm, the second arm, and the medial region, and wherein forming the pocket comprises forming the pocket such that the pocket is at least partially defined by the perimeter band.

22. The method of claim 21, wherein forming the pocket comprises forming the pocket such that the pocket is arranged to extend substantially perpendicularly to at least one of the first laterally-extending support surface and the opposing second laterally-extending support surface.

23. The method of claim 17, wherein forming the pocket comprises forming the pocket such that the pocket defines an opening configured to receive the thermal element therethrough.

24. The method of claim 23, wherein forming the pocket comprises arranging a closure about the opening of the pocket, the closure being configured to be manipulated about the opening to removably secure the thermal element within the pocket.

25. The method of claim 24, wherein arranging the closure comprises arranging the closure, comprising at least one of a magnet, a snap fastener, a zipper, and a hook and loop fastener, about the opening of the pocket.

* * * * *